(12) United States Patent
McCormack et al.

(10) Patent No.: US 9,622,874 B2
(45) Date of Patent: Apr. 18, 2017

(54) CERVICAL DISTRACTION/IMPLANT DELIVERY DEVICE

(71) Applicant: Providence Medical Technology, Inc., Lafayette, CA (US)

(72) Inventors: Bruce M. McCormack, San Francisco, CA (US); Jeffrey D. Smith, Lafayette, CA (US)

(73) Assignee: PROVIDENCE MEDICAL TECHNOLOGY, INC., Lafayette, CA (US)

(*) Notice: Subject to any disclaimer, the term of this patent is extended or adjusted under 35 U.S.C. 154(b) by 51 days.

(21) Appl. No.: 13/949,042

(22) Filed: Jul. 23, 2013

(65) Prior Publication Data
US 2013/0310878 A1  Nov. 21, 2013

Related U.S. Application Data

(63) Continuation of application No. 12/559,193, filed on Sep. 14, 2009, now Pat. No. 8,512,347, which is a
(Continued)

(51) Int. Cl.
*A61B 17/70* (2006.01)
*A61B 17/58* (2006.01)
(Continued)

(52) U.S. Cl.
CPC ............ *A61F 2/442* (2013.01); *A61B 17/025* (2013.01); *A61B 17/562* (2013.01);
(Continued)

(58) Field of Classification Search
CPC ............ A61B 17/7062; A61B 17/7064; A61B 17/7065
(Continued)

(56) References Cited

U.S. PATENT DOCUMENTS

| 1,934,962 A | 11/1933 | Barry |
| 2,708,376 A | 5/1955 | Booth |

(Continued)

FOREIGN PATENT DOCUMENTS

| DE | G93 04 368.6 | 5/2003 |
| FR | 2 722 980 A1 | 2/1996 |

(Continued)

OTHER PUBLICATIONS

Advisory Action, U.S. Appl. No. 12/317,682, dated Apr. 6, 2012, 3 pages.
(Continued)

*Primary Examiner* — Nicholas Woodall
(74) *Attorney, Agent, or Firm* — Dorsey & Whitney LLP

(57) ABSTRACT

Systems for distracting a facet joint and positioning a permanent implant in the joint are disclosed. The implants serve to retain a distracted position of the facet joint which is achieved with positioning of the leading end of a distraction tool in the facet joint and then distracting or enlarging the joint a desired amount. The permanent implant could be part of the distraction mechanism which can be separated from the delivery tool once the joint has been distracted or an auxiliary implant may be positioned before the distraction mechanism is removed from the distracted joint. The permanent implants can be solid, mechanical devices that may have fixation means thereon to hold them in place or injected fluids such as hydrogels or fluids confined within balloons.

16 Claims, 23 Drawing Sheets

Related U.S. Application Data continuation-in-part of application No. 12/455,814, filed on Jun. 5, 2009, now Pat. No. 8,361,152, which is a continuation-in-part of application No. 12/317,682, filed on Dec. 23, 2008, now Pat. No. 8,267,966.

(60) Provisional application No. 61/169,601, filed on Apr. 15, 2009, provisional application No. 61/109,776, filed on Oct. 30, 2008, provisional application No. 61/097,103, filed on Sep. 15, 2008, provisional application No. 61/059,723, filed on Jun. 6, 2008.

(51) Int. Cl.
*A61F 2/44* (2006.01)
*A61B 17/02* (2006.01)
*A61B 17/56* (2006.01)
*A61B 17/88* (2006.01)
*A61B 17/00* (2006.01)
*A61B 19/00* (2006.01)
*A61F 2/30* (2006.01)

(52) U.S. Cl.
CPC ...... *A61B 17/7062* (2013.01); *A61B 17/7064* (2013.01); *A61B 17/7065* (2013.01); *A61B 17/8822* (2013.01); *A61F 2/4405* (2013.01); *A61B 2017/00557* (2013.01); *A61B 2017/0256* (2013.01); *A61B 2019/307* (2013.01); *A61F 2002/30438* (2013.01); *A61F 2002/30579* (2013.01); *A61F 2002/30841* (2013.01); *A61F 2220/0041* (2013.01)

(58) Field of Classification Search
USPC .......................................... 606/90, 247–249
See application file for complete search history.

(56) References Cited

U.S. PATENT DOCUMENTS

| | | |
|---|---|---|
| 3,486,505 A | 12/1969 | Morrison et al. |
| 4,479,491 A | 10/1984 | Martin |
| 4,530,355 A | 7/1985 | Griggs |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber |
| 5,443,514 A | 8/1995 | Steffee |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich |
| 5,554,191 A | 9/1996 | Lahille et al. |
| 5,571,191 A | 11/1996 | Fitz |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz et al. |
| 5,895,426 A | 4/1999 | Scarborough et al. |
| 5,899,908 A | 5/1999 | Kuslich et al. |
| 5,928,238 A | 7/1999 | Scarborough et al. |
| 5,961,522 A | 10/1999 | Mehdizadeh |
| 5,976,146 A | 11/1999 | Ogawa et al. |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,149,650 A | 11/2000 | Michelson |
| RE37,005 E | 12/2000 | Michelson et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,248,110 B1 | 6/2001 | Reiley et al. |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Houfburg |
| 6,315,795 B1 | 11/2001 | Scarborough et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,530,955 B2 | 3/2003 | Boyle et al. |
| 6,565,574 B2 | 5/2003 | Michelson |
| 6,569,186 B1 | 5/2003 | Winters et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |

(56) References Cited

U.S. PATENT DOCUMENTS

| | | |
|---|---|---|
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,979,333 B2 | 12/2005 | Hammerslag |
| 7,001,385 B2 | 2/2006 | Bonutti |
| 7,008,453 B1 | 3/2006 | Michelson |
| 7,033,362 B2 | 4/2006 | McGahan et al. |
| 7,033,394 B2 | 4/2006 | Michelson |
| 7,066,961 B2 | 6/2006 | Michelson |
| 7,083,623 B2 | 8/2006 | Michelson |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,179,263 B2 | 2/2007 | Zdeblick et al. |
| 7,207,991 B2 | 4/2007 | Michelson |
| 7,220,280 B2 | 5/2007 | Kast et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,500,992 B2 | 3/2009 | Li |
| 7,517,358 B2 | 4/2009 | Petersen |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,632,291 B2 | 12/2009 | Stephens et al. |
| 7,641,664 B2 | 1/2010 | Pagano |
| 7,648,523 B2 | 1/2010 | Mirkovic et al. |
| 7,655,027 B2 | 2/2010 | Michelson |
| 7,662,173 B2 | 2/2010 | Cragg et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| 7,708,761 B2 | 5/2010 | Petersen |
| 7,722,619 B2 | 5/2010 | Michelson |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| 7,789,898 B2 | 9/2010 | Peterman |
| 7,824,431 B2 | 11/2010 | McCormack et al. |
| 7,837,713 B2 | 11/2010 | Petersen |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| 7,879,098 B1 | 2/2011 | Simmons |
| 7,887,565 B2 | 2/2011 | Michelson |
| 7,892,286 B2 | 2/2011 | Michelson |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,062,303 B2 | 11/2011 | Berry et al. |
| 8,066,705 B2 | 11/2011 | Michelson |
| 8,097,034 B2 | 1/2012 | Michelson |
| 8,100,944 B2 | 1/2012 | Lauryssen et al. |
| 8,118,838 B2 | 2/2012 | Winslow et al. |
| 8,128,660 B2 | 3/2012 | Mitchell et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,197,513 B2 | 6/2012 | Fisher et al. |
| 8,267,966 B2 | 9/2012 | McCormack et al. |
| 8,348,979 B2 | 1/2013 | McCormack |
| 8,361,152 B2 | 1/2013 | McCormack et al. |
| 8,394,107 B2 | 3/2013 | Fanger et al. |
| 8,425,558 B2 | 4/2013 | McCormack et al. |
| 8,512,347 B2 | 8/2013 | McCormack et al. |
| 8,668,722 B2 | 3/2014 | Pavlov et al. |
| 8,753,347 B2 | 6/2014 | Mccormack et al. |
| 8,764,755 B2 | 7/2014 | Michelson |
| 8,828,062 B2 | 9/2014 | Mccormack et al. |
| D723,690 S | 3/2015 | Mccormack et al. |
| D723,691 S | 3/2015 | Mccormack et al. |
| 8,998,905 B2 | 4/2015 | Marik et al. |
| 9,011,492 B2 | 4/2015 | Mccormack et al. |
| D745,156 S | 12/2015 | Mccormack et al. |
| 9,211,198 B2 | 12/2015 | Michelson |
| 9,220,608 B2 | 12/2015 | Mckay |
| 9,271,765 B2 | 3/2016 | Blain |
| 9,333,086 B2 | 5/2016 | Mccormack et al. |
| 2002/0026195 A1 | 2/2002 | Layne et al. |
| 2002/0107519 A1 | 8/2002 | Dixon |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2003/0028251 A1 | 2/2003 | Mathews |
| 2003/0105526 A1 | 6/2003 | Bryant et al. |
| 2003/0139816 A1 | 7/2003 | Michelson |
| 2003/0149438 A1 | 8/2003 | Nichols et al. |
| 2003/0225416 A1 | 12/2003 | Bonvallet et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochschuler et al. |
| 2005/0015149 A1 | 1/2005 | Michelson |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1 | 6/2005 | Chappuis |
| 2005/0159650 A1 | 7/2005 | Raymond et al. |

(56) References Cited

U.S. PATENT DOCUMENTS

| | | |
|---|---|---|
| 2005/0159746 A1 | 7/2005 | Grob et al. |
| 2005/0182417 A1 | 8/2005 | Pagano |
| 2005/0216018 A1 | 9/2005 | Sennett |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0015184 A1 | 1/2006 | Winterbottom et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0079905 A1 | 4/2006 | Beyar et al. |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1* | 5/2006 | Petersen ............. 623/17.11 |
| 2006/0149289 A1 | 7/2006 | Winslow et al. |
| 2006/0184172 A1 | 8/2006 | Michelson |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0206118 A1 | 9/2006 | Kim et al. |
| 2006/0235391 A1 | 10/2006 | Sutterlin, III |
| 2006/0241626 A1 | 10/2006 | McGahan et al. |
| 2006/0241758 A1 | 10/2006 | Peterman et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0123888 A1 | 5/2007 | Bleich et al. |
| 2007/0135814 A1 | 6/2007 | Farris |
| 2007/0135921 A1 | 6/2007 | Park |
| 2007/0150061 A1 | 6/2007 | Trieu |
| 2007/0161991 A1 | 7/2007 | Altarac et al. |
| 2007/0179617 A1 | 8/2007 | Brown et al. |
| 2007/0225721 A1 | 9/2007 | Thelen et al. |
| 2007/0225812 A1 | 9/2007 | Gill |
| 2007/0276491 A1 | 11/2007 | Ahrens et al. |
| 2007/0282441 A1 | 12/2007 | Stream et al. |
| 2007/0288014 A1 | 12/2007 | Shadduck et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0065219 A1 | 3/2008 | Dye |
| 2008/0108996 A1 | 5/2008 | Padget et al. |
| 2008/0140207 A1 | 6/2008 | Olmos et al. |
| 2008/0161810 A1 | 7/2008 | Melkent |
| 2008/0161929 A1 | 7/2008 | McCormack et al. |
| 2008/0167657 A1 | 7/2008 | Greenhalgh |
| 2008/0177311 A1 | 7/2008 | Winslow et al. |
| 2008/0216846 A1 | 9/2008 | Levin |
| 2008/0234677 A1 | 9/2008 | Dahners et al. |
| 2008/0255564 A1 | 10/2008 | Michelson |
| 2008/0255622 A1 | 10/2008 | Mickiewicz et al. |
| 2008/0255667 A1 | 10/2008 | Horton |
| 2008/0287955 A1 | 11/2008 | Michelson |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0275994 A1 | 11/2009 | Phan et al. |
| 2010/0069912 A1 | 3/2010 | McCormack et al. |
| 2010/0086185 A1 | 4/2010 | Weiss |
| 2010/0093829 A1 | 4/2010 | Gorman |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0082548 A1 | 4/2011 | Assell et al. |
| 2012/0143334 A1 | 6/2012 | Boyce et al. |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0123922 A1 | 5/2013 | McCormack et al. |
| 2013/0144389 A1 | 6/2013 | Bonutti |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2014/0025113 A1 | 1/2014 | McCormack et al. |
| 2014/0100657 A1 | 4/2014 | McCormack et al. |

FOREIGN PATENT DOCUMENTS

| | | |
|---|---|---|
| WO | WO 99/49818 A1 | 10/1999 |
| WO | 00/35388 | 6/2000 |
| WO | WO 00/35388 A1 | 6/2000 |
| WO | WO 00/53126 A1 | 9/2000 |
| WO | WO 01/01895 A1 | 1/2001 |
| WO | 02/038062 | 5/2002 |
| WO | 02/38062 | 5/2002 |
| WO | WO 02/34120 A2 | 5/2002 |
| WO | WO 02/38062 A2 | 5/2002 |
| WO | 02/076335 | 10/2002 |
| WO | 02076335 | 10/2002 |
| WO | WO 02/076335 A2 | 10/2002 |
| WO | WO 2006/058221 A2 | 6/2006 |
| WO | WO 2006/130791 A2 | 12/2006 |

OTHER PUBLICATIONS

Amendment and Response to Office Action, U.S. Appl. No. 12/110,548, filed May 5, 2009, 11 pages.

Amendment, U.S. Appl. No. 11/618,619, filed May 5, 2008, 10 pages.

Corrected Response to Restriction Requirement, U.S. Appl. No. 12/317,682, filed Sep. 2, 2011, 15 pages.

Final Office Action, U.S. Appl. No. 11/618,619, mailed Aug. 8, 2008, 10 pages.

Final Office Action, U.S. Appl. No. 12/110,548, mailed Feb. 26, 2010, 4 pages.

Final Office Action, U.S. Appl. No. 12/317,682, mailed Feb. 10, 2012, 8 pages.

Final Office Action, U.S. Appl. No. 12/559,193, mailed Feb. 13, 2013, 10 pages.

Final Office Action, U.S. Appl. No. 12/653,283, mailed Mar. 21, 2012, 8 pages.

Final Office Action, U.S. Appl. No. 12/653,283, mailed Nov. 19, 2012, 8 pages.

Goel, Atul et al., Facetal Distraction as Treatment for Single- and Multilevel Cervical spondylotic Radiculopathy and Myelopathy: A Preliminary Report. J Neurosurg Spine 14:689-696, Jun. 2011; published online Mar. 18, 2011; DOI: 10.3171/2011.2.SPINE10601.

International Search Report and Written Opinion, International patent application No. PCT/US07/89146 Nov. 3, 2008.

International Search Report and Written Opinion, International patent application No. PCT/US2009/030461, dated Aug. 17, 2009.

International Search Report and Written Opinion, International patent application No. PCT/US2009/003423, dated Dec. 14, 2009.

International Search Report and Written Opinion, International patent application No. PCT/US2009/056841, dated Apr. 9, 2010.

(56) References Cited

OTHER PUBLICATIONS

International Search Report and Written Opinion, PCT/US2009/006478, dated Jun. 29, 2010.
Interview summary, U.S. Appl. No. 11/618,619, mailed Mar. 18, 2008, 3 pages.
Non-Final Office Action, U.S. Appl. No. 11/618,619, mailed Jan. 3, 2008, 12 pages.
Non-Final Office Action, U.S. Appl. No. 12/110,548, mailed Feb. 17, 2009, 11 pages.
Nonfinal Office Action, U.S. Appl. No. 12/317,682, dated Sep. 15, 2011, 25 pages.
Non-Final Office Action, U.S. Appl. No. 12/559,193, mailed Sep. 18, 2012, 26 pages.
Non-Final Office Action, U.S. Appl. No. 12/653,283, mailed Feb. 10, 2012, 7 pages.
Non-Final Office Action, U.S. Appl. No. 12/653,283, mailed Jul. 18, 2012, 5 pages.
Nonfinal Office Action, U.S. Appl. No. 12/653,283, dated Aug. 9, 2011, 20 pages.
Non-Final Office Action, U.S. Appl. No. 12/889,122, dated Mar. 29, 2012, 20 pages.
Notice of Allowance, U.S. Appl. No. 12/110,548, mailed Mar. 29, 2010, 5 pages.
Notice of Allowance, U.S. Appl. No. 12/110,548, mailed Jul. 14, 2010, 10 pages.
Notice of Allowance, U.S. Appl. No. 12/317,682, mailed May 11, 2012, 10 pages.
Notice of Allowance, U.S. Appl. No. 12/559,193, mailed Apr. 22, 2013, 8 pages.
Notice of Allowance, U.S. Appl. No. 12/653,283, mailed Feb. 28, 2013, 10 pages.
Notice of Allowance, U.S. Appl. No. 12/889,122, mailed Sep. 25, 2012, 7 pages.
Notice of Non-Responsive Amendment, U.S. Appl. No. 12/317,682, dated Aug. 8, 2011, 2 pages.
Office Action (Quayle), U.S. Appl. No. 12/653,283, dated Dec. 22, 2011, 8 pages.
Office Action (Restriction), U.S. Appl. No. 12/317,682, dated Apr. 22, 2011, 14 pages.
Office Action (Restriction), U.S. Appl. No. 12/653,283, dated Jun. 24, 2011, 9 pages.
Partial International Search Report, International patent application No. PCT/US2009/030461, dated May 13, 2009.
Partial International Search Report, International patent application No. PCT/US2009/003423, dated Sep. 14, 2009.
Partial International Search Report, International patent application No. PCT/US2009/056841, dated Dec. 10, 2009.
Press Release, Interventional Spine, Inc., FDA Grants Conditional Approval to Interventional Spine's PercuDyn System IDE Application (Jul. 1, 2008).
Press Release, Interventional Spine, Inc., Interventional Spine, Inc. Introduces the PERPOS Fusion Facet Prep Kit (Oct. 14, 2008).
Press Release, minSURG Corp., Orthopedic Development Corporation's TruFUSE Procedure Tops 1,750 Patients in First Year (Sep. 24, 2007).
Response to Advisory Action, U.S. Appl. No. 12/317,682, filed Apr. 24, 2012, 4 pages.
Response to Final Office Action, U.S. Appl. No. 12/317,682, filed Mar. 22, 2012, 17 pages.
Response to Final Office Action, U.S. Appl. No. 12/559,193, filed Apr. 12, 2013, 8 pages.
Response to Final Office Action, U.S. Appl. No. 12/653,283, filed Jun. 15, 2012, 7 pages.
Response to Final Office Action, U.S. Appl. No. 12/653,283, filed Feb. 19, 2013, 5 pages.
Response to Non-Final Office Action and Terminal Disclaimer, U.S. Appl. No. 12/889,122, filed Jun. 27, 2012, 8 pages.
Response to Non-Final Office Action, U.S. Appl. No. 12/317,682, filed Dec. 13, 2011, 19 pages.
Response to Non-Final Office Action, U.S. Appl. No. 12/599,193, filed Dec. 13, 2012, 7 pages.
Response to Non-Final Office Action, U.S. Appl. No. 12/653,283, filed Dec. 6, 2011, 14 pages.
Response to Non-Final Office Action, U.S. Appl. No. 12/653,283, filed Mar. 8, 2012, 9 pages.
Response to Non-Final Office Action, U.S. Appl. No. 12/653,283, filed Oct. 18, 2012, 6 pages.
Response to Quayle Action, U.S. Appl. No. 12/653,283, filed Feb. 1, 2012, 3 pages.
Response to Restriction, U.S. Appl. No. 12/317,682, filed May 16, 2011, 15 pages.
Response to Restriction, U.S. Appl. No. 12/559,193, filed Jul. 17, 2012, 6 pages.
Response to Restriction, U.S. Appl. No. 12/653,283, filed Jul. 22, 2011, 8 pages.
Response to Restriction, U.S. Appl. No. 13/614,372, filed May 16, 2013, 6 pages.
Response to Restriction, U.S. Appl. No. 13/614,508, filed Jun. 1, 2013, 6 pages.
Response to Restriction, U.S. Appl. No. 13/614,577, filed Jun. 1, 2013, 6 pages.
Response to Restriction, U.S. Appl. No. 13/627,825, filed Jun. 1, 2013, 6 pages.
Response to Restriction, U.S. Appl. No. 13/627,850, filed Jun. 1, 2013, 5 pages.
Response to Restriction, U.S. Appl. No. 13/627,865, filed Jun. 1, 2013, 6 pages.
Restriction Requirement, U.S. Appl. No. 12/559,193, dated Apr. 18, 2012, 10 pages.
Restriction Requirement, U.S. Appl. No. 13/614,372, mailed Apr. 17, 2013, 6 pages.
Restriction Requirement, U.S. Appl. No. 13/614,508, mailed May 3, 2013, 6 pages.
Restriction Requirement, U.S. Appl. No. 13/614,577, mailed May 22, 2013, 6 pages.
Restriction Requirement, U.S. Appl. No. 13/627,825, mailed May 2, 2013, 7 pages.
Restriction Requirement, U.S. Appl. No. 13/627,850, mailed May 2, 2013, 7 pages.
Restriction Requirement, U.S. Appl. No. 13/627,865, mailed May 6, 2013, 5 pages.
U.S. Appl. No. 29/435,381, filed Oct. 23, 2012, McCormack et al.
U.S. Appl. No. 29/435,385, filed Oct. 23, 2012, McCormack et al.
Atul Goel, Facetal distraction as treatment for single- and multilevel cervical spondylotic radiculopathy and myelopathy: a preliminary report, J Neurosurg Spine, Jun. 2011, pp. 689-696.
Goel, Atul, "Facetal distraction as treatment for single- and multi-level cervical spondylotic radiculopathy and myelopathy: a preliminary report," J Neurosurg Spine, Jun. 2011, pp. 689-696.

* cited by examiner

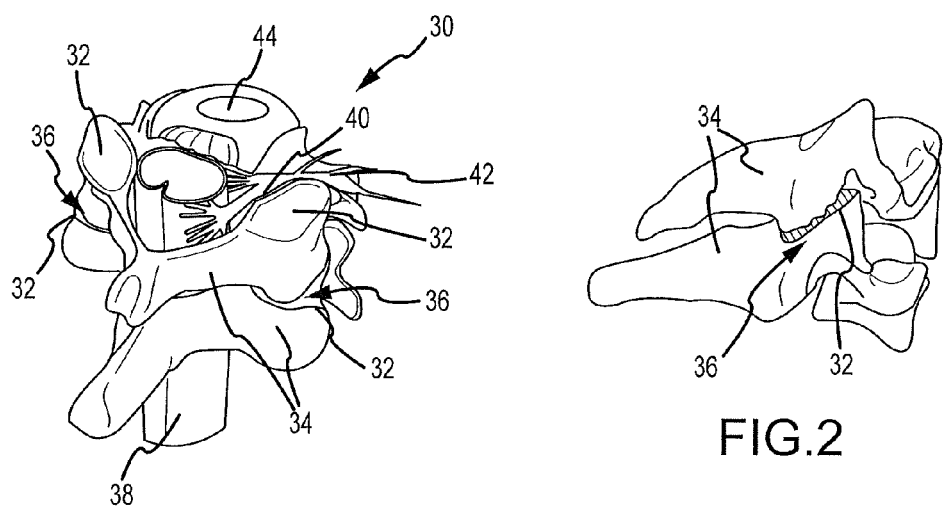
FIG.1
FIG.2
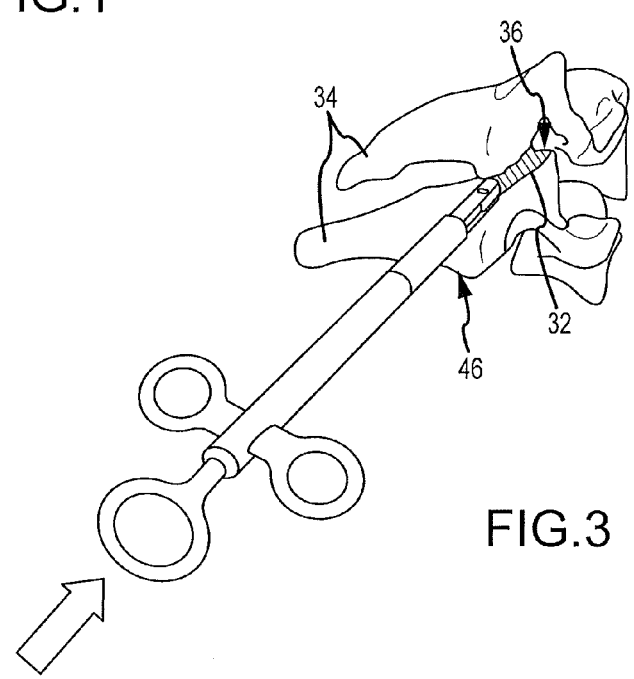
FIG.3

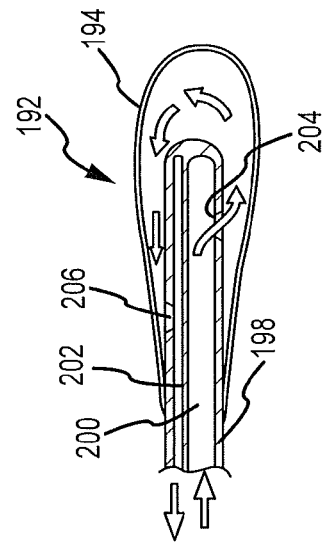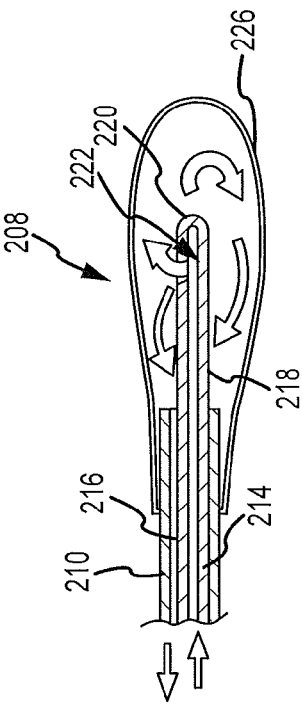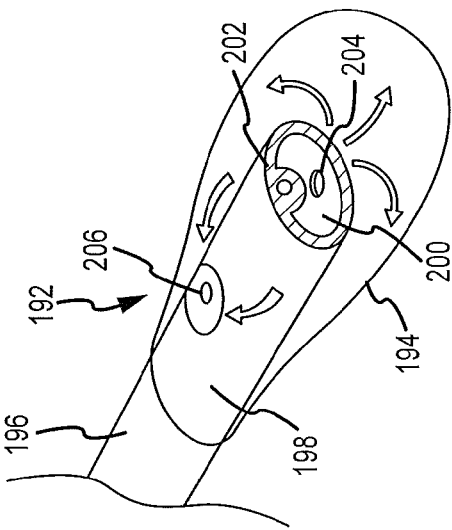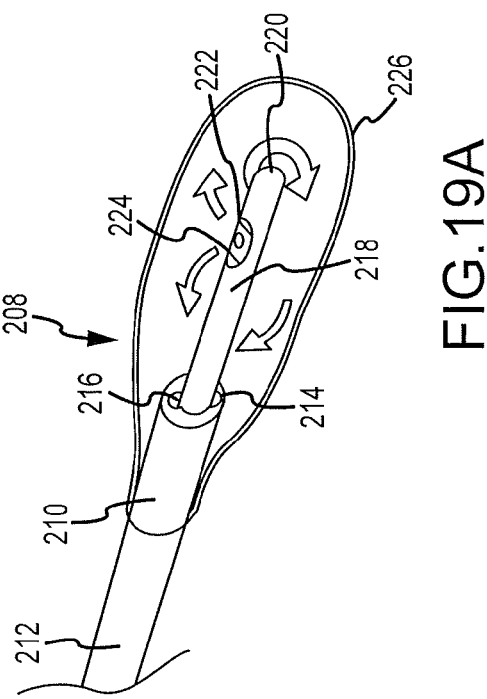

CERVICAL DISTRACTION/IMPLANT DELIVERY DEVICE

CROSS REFERENCE TO RELATED APPLICATION

The present application is a continuation of U.S. application Ser. No. 12/559,193 filed Sep. 14, 2009 and entitled Cervical Distraction/Implant Delivery Device (the '193 application). The '193 application is a continuation-in-part of U.S. application Ser. No. 12/455,814 filed Jun. 5, 2009, now U.S. Pat. No. 8,361,152, and entitled Facet Joint Implants and Delivery Tools (the '814 application). The '814 application is a continuation-in-part of U.S. application Ser. No. 12/317,682 filed Dec. 23, 2008, now U.S. Pat. No. 8,267,966, and entitled Facet Joint Implants and Delivery Tools (the '682 application).

The '193 application also claims priority from: U.S. Provisional Application No. 61/169,601 filed Apr. 15, 2009 and entitled Facet Joint Implants and Delivery Tools; U.S. Provisional Application No. 61/109,776 filed Oct. 30, 2008 and entitled Facet Joint Implants; and U.S. Provisional Application No. 61/097,103 filed Sep. 15, 2008 and entitled Cervical Distraction/Implant Delivery Device.

The '682 application claims priority from U.S. Provisional Application No. 61/059,723 filed Jun. 6, 2008 and entitled Spine Distraction Device.

The contents of all of the above applications are hereby incorporated by reference herein in their entireties.

BACKGROUND OF THE INVENTION

Field of the Invention

This invention pertains generally to a cervical distraction device and more particularly to such a device that cannot only distract a facet joint but also deliver an implant to the distracted joint.

Description of the Relevant Art

Chronic back problems cause pain and disability for a large segment of the population. Adverse spinal conditions are characteristic of age. With aging, generally comes an increase in spinal stenosis (including, but not limited to, central canal and lateral stenosis), and facet arthropathy. Spinal stenosis results in a reduction of foraminal area (i.e. the available space for the passage of nerves and blood vessels), which compresses the cervical nerve roots and causes radicular pain. Extension and ipsilateral rotation of the neck further reduces the foraminal area and contributes to pain, nerve root compression, and neural injury. However, neck flexion generally increases the foraminal area.

Cervical disc herniations predominantly present upper extremity radicular symptoms. The vast majority of these herniations do not have an associated neurological deficit and present pain only. A well-described treatment for cervical disc herniations is closed traction. There are a number of marketed devices that alleviate pain by pulling on the head to increase foraminal height.

Cervical disc herniations have been treated with anterior and posterior surgery. The vast majority of these surgeries are performed through an anterior approach, which requires a spinal fusion. These surgeries are expensive and beget additional surgeries due to change in biomechanics of the neck. There is a three percent incidence of re-operation after cervical spine surgery.

It is an object of the present invention to provide a minimally invasive device and procedure to increase foraminal height to reduce radicular symptoms for patients with disc herniations.

SUMMARY OF THE INVENTION

In one embodiment, a distraction tool for distracting a facet joint can include a handle, a cannula extending from the handle, and a distraction mechanism positioned on a distal end of the cannula and adapted to be placed in the facet joint. In this embodiment, the handle can be in communication with the distraction mechanism and actuation of the handle can cause distraction thereof.

In another embodiment, a distraction mechanism for distracting a facet joint can be provided. The mechanism can include a head in the form of an oblong band and an elongate member extending through the head. The elongate member can be adapted to draw opposing ends of the head toward one another thereby expanding the head.

In still another embodiment, a distraction mechanism can include a plurality of pairs of teeth in pivotal relation with a central core and an elongate member extending through the central core. Actuation of the elongate member can cause distraction of at least one of the plurality of pairs of teeth.

In still another embodiment, a distraction mechanism can include a hollow elongated body having facet engaging features and an elongated member adapted for insertion within the body. Insertion of the elongated member can actuate the facet engaging features.

In still another embodiment, a distraction mechanism can include an expandable receiving portion having upper and lower generally planar elements connected at an end with a living hinge. The distraction mechanism can also include an actuation device adapted to be placed between the planar elements. The planar elements can include malleable material that conforms to the facet surface upon implantation.

In yet another embodiment, a delivery tool for positioning a distraction mechanism in a facet joint can include a distraction mechanism for distracting a facet joint and a handle and a cannula connected to one another and carrying said distraction mechanism on a distal end thereof. The handle can include means for delivering energy to said distraction mechanism, and said distraction mechanism can be manipulatable to increase the spacing of said confronting facets thereby distracting said facet joint.

A device and technique are disclosed for a minimally invasive surgical implantation to reduce radicular symptoms by inserting a distraction mechanism in a facet joint of an affected level of the spine to preserve the physiology of the spine. In particular, embodiments of the present invention provide for distracting and translating the cervical spine to increase the foraminal dimension in extension and neutral positions. The distraction mechanism may have a portion which can serve as an implant or it may be a mechanism for facilitating insertion of a separate implant. When the distraction mechansim is positioned in the cervical facet joint, it expands to distract or increase the space between the vertebrae to increase the foraminal area or dimension and reduce pressure on the nerves and blood vessels of the cervical spine. The devices and techniques disclosed supplement those disclosed in U.S. nonprovisional patent application Ser. No. 11/618,619 filed Dec. 29, 2006, entitled Cervical Distraction Device, and U.S. provisional patent application Ser. No. 61/059,723, filed Jun. 6, 2008, entitled Spine Distraction Device, which are of common ownership with the present application, the disclosures of which are hereby incorporated by reference.

The implantation procedure may be performed under conscious sedation in order to obtain intra-operative patient symptom feedback.

After achieving the desired distraction of the facet joint, the distal tip of the distraction tool may be detached from the tool so the distraction device itself serves as a permanent implant for placement in the facet joint. The patient is left with the distraction device implant in the facet joint with permanent increased foraminal height. As an alternative, the distraction device can be removed from the distracted joint after a separate or auxiliary insert is positioned in the joint.

While the implant may comprise an inflatable balloon configured to be filled with an inflation medium, e.g. hydrogel or the like, to distribute a compressive load on the articulating surfaces as disclosed in the aforenoted U.S. nonprovisional patent application Ser. No. 11/618,619, pursuant to the present invention, the implant may also be a mechanical device that does or does not expand or inflate.

The implant is configured to dynamically stabilize or fuse the facet joint and retain it in an expanded or distracted condition. The implant maintains a minimal distance between the articulating surfaces and, in some embodiments, allows motion of a first vertebra with respect to a second adjacent vertebra.

According to the technique of the invention, an expandable or non-expandable distraction device is inserted in a collapsed state into a facet joint bounded by first and second vertebrae, and is expanded within the facet joint to increase a foraminal dimension associated with the first and second vertebrae. The implant is installed in a facet joint located between adjacent cervical vertebrae. The expandable implant engages the articulating surfaces of the facet joint to increase the distance between the articulating surfaces.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

FIG. 1 is a fragmentary isometric of a portion of the human spine showing a facet joint which may be treated with the devices and techniques of the present invention to distract the facet joint and retain it in an expanded condition.

FIG. 2 is an isometric similar to FIG. 1 viewed from a different direction.

FIG. 3 is an isometric similar to FIG. 2 with a distraction device in accordance with the present invention having its distal end inserted into the facet joint and having an implant device releasably held in the distal end.

FIG. 18A is a diagrammatic fragmentary isometric with parts removed illustrating a thirteenth embodiment of the present invention.

FIG. 18B is a fragmentary diagrammatic vertical section through the device shown in FIG. 18A.

FIG. 19A is a fragmentary diagrammatic similar to FIG. 18A showing an alternative fourteenth embodiment.

FIG. 19B is a fragmentary vertical section similar to FIG. 18B showing the alternative embodiment of FIG. 19A.

DETAILED DESCRIPTION OF THE INVENTION

Figure 4:
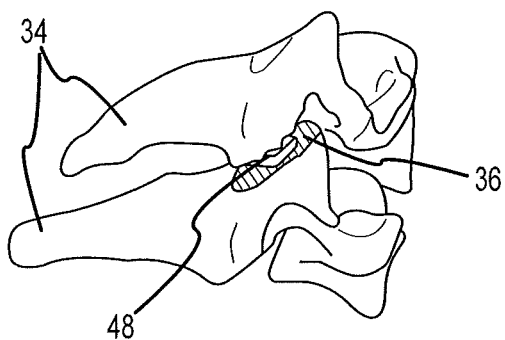
FIG. 4 is an isometric similar to FIG. 3 with the implant having been positioned within the facet joint to retain the distracted position of the joint.

Pursuant to the present invention, devices and techniques for distracting and retaining a facet joint in a distracted and forwardly translated condition are disclosed. Prior to distracting the facet joint, the joint, which can be difficult to access, can be accessed pursuant, for example, to the method and apparatus disclosed in U.S. Non-provisional application Ser. No. 12/350,609, filed Jan. 8, 2009, which is commonly owned with the present application and hereby incorporated by reference. Pursuant to the disclosure in that application, the access system is comprised of one or more cannulas made of steel, titanium, or plastic. The initial facet joint access cannula can have a sharp spatula tip on the distal end. The spatula tip can have a flat configuration to enable access into the flat facet joint. Once the spatula tip achieves access into the generally flatly oriented facet joint, subsequent stylets and working instruments can be passed down this access channel to complete a distraction procedure. The distraction procedure can be accomplished with devices and techniques to be described hereafter.

The percutaneous distraction mechanism can be introduced down the working cannula of the above-identified access system. The mechanism can be part of a delivery tool that would allow the surgeon to generate distraction by applying energy to a handle of the delivery tool for the distraction mechanism positioned at the distal end of the tool. The handle of the delivery tool can be configured in any number of ways including but not limited to the following:

a) Trigger grip—index finger activates distraction by pulling the trigger to apply energy to the distraction mechanism.

b) Scissor grip—index and middle fingers meet and separate to apply energy to the distraction mechanism.

c) Thumb wheel or slide'thumb rolls a wheel or slides a slide that progressively applies more energy to the distraction mechanism.

d) Thumb cushion rod—thumb plunges a stylet down the working cannula to apply energy to the distraction mechanism.

e) Stylet screwdriver—stylet is threaded down the working cannula into the distraction mechanism applying increasingly more energy to the distraction mechanism as the stylet screwdriver advances.

f) Mallet based handle—a stylet with a flat malleable surface is inserted for the purposes of receiving and dispersing mallet energy and applying it to the distraction mechanism.

g) Thumb button—a button on the proximal end of the handle is pushed which creates one of a number of mechanical systems to apply energy to the distraction mechanism. Those mechanical systems could include but are not limited to:

i) hydraulic pressure generation;
ii) mechanical drill;
iii) level system; or
iv) elastic bands with "rope and pulley" mechanism.

h) Wedge firestarter—triangular wedge located at the proximal end of the tool is flattened to generate energy to apply to the distraction mechanism.

i) Foot or hand pump—feet or hands of surgeon used to press the system to create energy to be applied to the distraction mechanism.

Referring to FIGS. 1-5, a description relating to any and/or all of the delivery tools and associated distraction mechanisms and implants disclosed herein is presented. Referring first to FIG. 1, a portion of a spinal column 30 is shown having facets 32 on vertebrae 34 and with facet joints 36 between adjacent facets 32 of the vertebrae 34. The spinal cord 38, of course, passes vertically through the aligned vertebrae 34 with peripheral nerves 40 passing from the spinal cord 38 outwardly through the spinal column 30 through foraminal openings 42 to predestined locations in the human body. When facet joints 36 become narrowed, usually from disc degeneration, the foraminal openings 42 are reduced in size pinching the nerve and causing pain to the individual.

Figure 5:
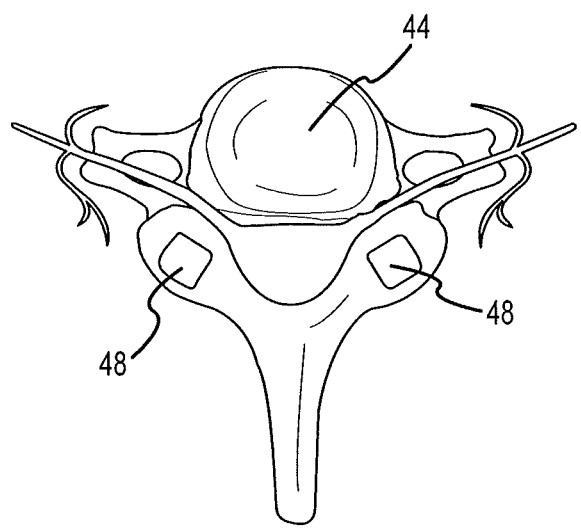
FIG. 5 is a section taken through the spinal column showing implant in position on bilateral facets.

Pursuant to the present invention, the facet joint 36, for example as shown in FIG. 2, can be accessed using a system, for example, of the type described in the aforenoted U.S. Non-provisional patent application Ser. Nos. 11/618,619 and 12/350,609, and after gaining access to the facet joint 36, a delivery tool 46 shown by way of example in FIG. 3, can have its distal end inserted into the facet joint 36 and by expanding a distraction mechanism at the distal tip of the tool 46, the facet joint 36 can be distracted or enlarged. The distraction mechanism itself can be detachable from the tool 46 and left in the facet joint 36 as an implant or a separate implant can be inserted with the delivery tool 46 or otherwise once the joint 36 has been distracted. Accordingly, it is noted that while the tools herein are referred to as delivery tools because they may be used to deliver a distraction mechanism, the distraction mechanism may or may not be the resulting implant. FIG. 4 shows from a lateral location an implant 48 positioned in a facet joint 36 which holds the joint 36 in a distracted condition, while FIG. 5 is a plan view showing implants in position on facets 32 of a vertebra 34.

Figure 6A:
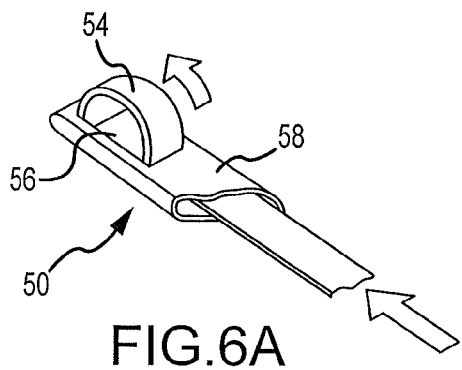
FIG. 6A is an isometric section with parts removed of a first embodiment of a distraction device in accordance with the present invention.
Figure 6B:
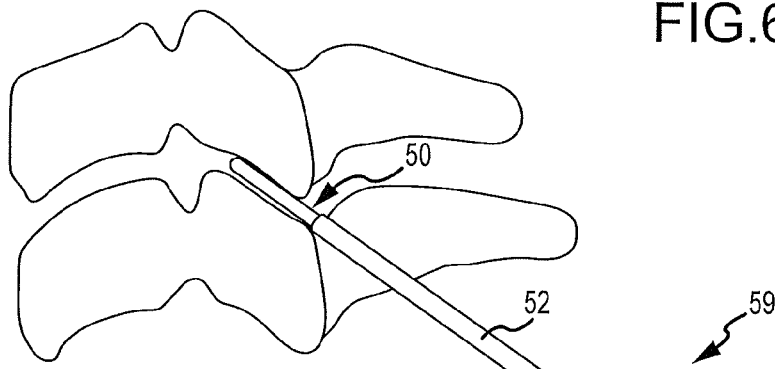
FIG. 6B is a diagrammatic side elevation of the device of FIG. 6A with the distal tip of the device positioned within a facet joint.
Figure 6C:
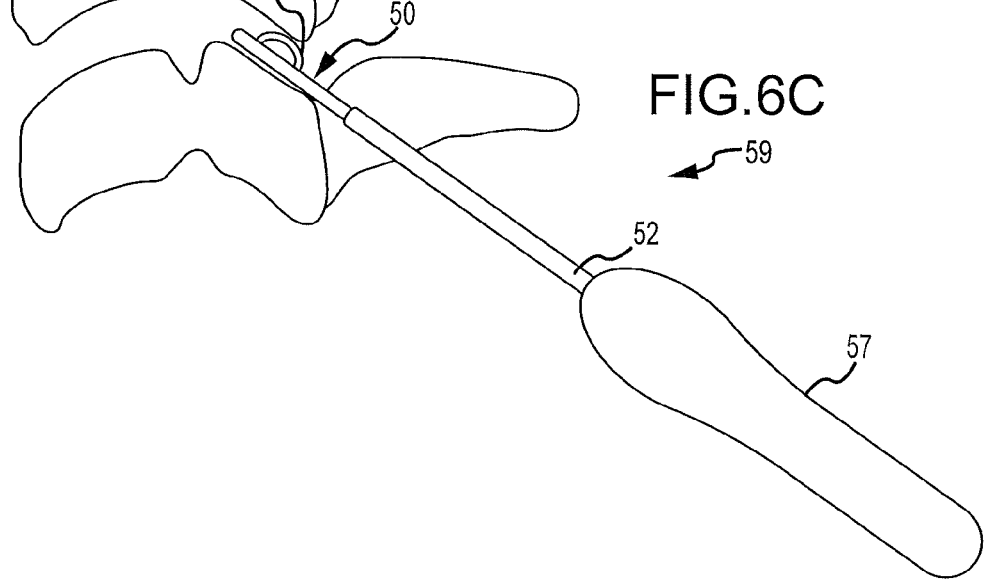
FIG. 6C is an elevation similar to FIG. 6B with the device expanded to distract the facet joint.

A first embodiment of a delivery tool 59 in accordance with the present invention is shown in FIGS. 6A-6C. It will there be seen, pursuant to the above description with any and/or all of the embodiments of the present invention to be disclosed hereafter, a delivery tool can be inserted down the working cannula, for example of the access system described previously, which can be docked in a facet joint 36. The distal end of the delivery tool can be positioned at the anterior aspect of the joint 36 and the surgeon can apply energy to the delivery tool to create separation and distraction of the facet joint 36. The separation can occur in both the vertical and horizontal planes of the joint 36 resulting in vertical distraction and forward/anterior translation of the superior vertebrae relative to the inferior vertebrae. The facet joint distraction and forward translation can cause an increase in foraminal area and thus reduce nerve root compression and associated symptoms.

Referring to the first embodiment of the invention shown in FIGS. 6A-6C, a delivery tool 59 can include a handle 57, a distraction cannula 52, and a distraction mechanism 50. The handle portion 57 can include any of the energy delivering handles described above. The handle 57 can be connected to the cannula 52 and the distraction mechanism 50 positioned within the cannula 52. The handle 57 can be configured to actuate the distraction mechanism 50.

The distraction mechanism 50 can be positioned at the tip of the delivery tool 59 and can include a band 54 of a somewhat rigid material that can be flexed so as to expand and become tall and generally flattened as it exits a rectangular opening 56 in the wall 58 of the distraction mechanism 50. The proximal end of the band 54 can be moveable and the distal end can be restrained. The rectangular opening 56, and thus the corresponding protruding band 54 can be smaller in length and width than the dimensions of the facet joint 36 being treated. The band 54 can be made of titanium, carbon, PEEK, nitinol, allograft, polymer, or plastic. Other elastic materials can be used.

In use, the handle 57 can be actuated thereby advancing the band 54. The force on the band 54 together with the restrained distal end of the band 54 can cause the band 54 to change its shape and configuration. That is, the compression developed in the band 54 can cause it to buckle out of plane and bow upwardly through the opening 56 and allow it to flatten out or conform to surface profile of the articular surface of the superior facet. While the band 54 may be sufficiently flexible to bow under compression, it may be sufficiently rigid to apply energy or force to the contacted articular surface. This applied force can result in the distraction and forward translation of the joint 36.

In one embodiment, the distraction mechanism 50, once expanded, can be separated from the cannula 52 and remain in place as an implant to retain the expanded condition of the facet joint 36. This may occur by way of a circumferential perforation between the cannula 52 and the distraction mechanism 50 just proximal to the opening 56. A release latch can also be provided between the cannula 52 and the distraction mechanism 50. Accordingly, the cannula 52 can be released from the distraction mechanism 50 and handle 57 and cannula 52 can be removed leaving the distraction mechanism 50 behind. In an alternative embodiment, a separate implant of the types to be described hereafter in other embodiments of the invention could be positioned in the distracted facet joint 36 before the distraction device was removed.

Figure 7A:
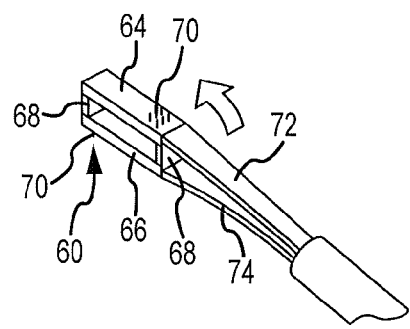
FIG. 7A is a fragmentary isometric of a second embodiment of the distraction device of the present invention.
Figure 7B:
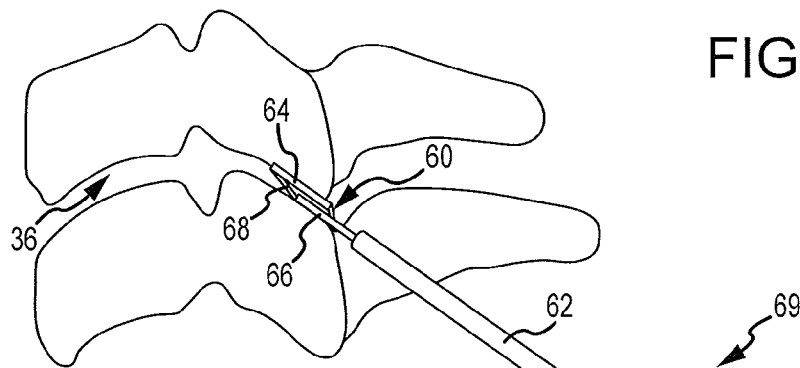
FIG. 7B is a side elevation of the device of FIG. 7A having its distal tip of the device inserted into a facet joint.
Figure 7C:
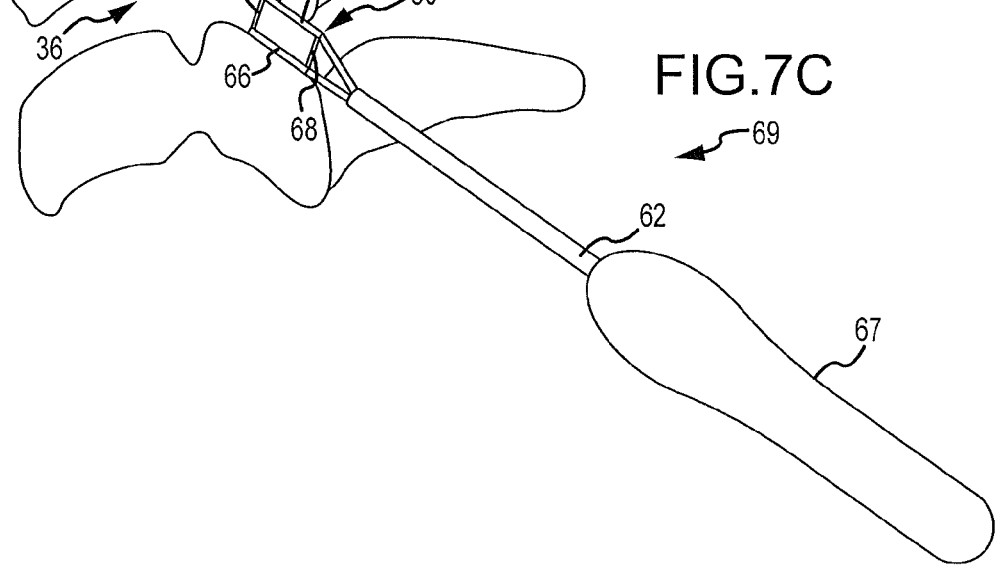
FIG. 7C is an elevation similar to FIG. 7B with the distal tip expanded to distract the facet joint.

A second embodiment of the invention is shown in FIGS. 7A-7C. A handle 67 and cannula 62 can be provided as described previously. In this embodiment, a distraction mechanism 60 in the form of a collapsible box can be positioned on the distal end of the delivery tool 69. The distraction mechanism 60 can include upper 66 and lower 64 walls as well as end walls 68 with the walls 64, 66, 68 being pivotally connected so the device is movable between a flattened position as shown in FIG. 7B to an expanded position as shown in FIG. 7A. A locking mechanism can also be provided such as a cross-brace or other device for maintaining the mechanism 60 in an expanded position once expanded.

Fixation mechanisms 70 can be provided on the exterior surface of both upper 64 and lower 66 walls. These fixation mechanisms 70 can be in the form of 1) Aggressive shark teeth, 2) Cleats, and/or 3) Roughened pores. The aggressive shark teeth (as shown in FIG. 7A) can have a directional orientation positioned to achieve optimal fixation relative to the natural biomechanics of various sections of the spine. The teeth can be long enough to gain purchase in the cortical bone of the facet surfaces. The cleats can have a less aggressive profile than the shark teeth but still allow for directional orientation for the same reasons described above. These cleats can also be capable of anchoring in the hard cortical bone of the facet surface. The roughened pores be positioned on the surface and can be adapted to prevent free sliding of the facet joint 36. These surfaces can be roughened and coated with FDA master file approved resurfacing chemicals that create friction and prevent device migration.

The collapsible box can be made of titanium, steel, carbon, PEEK, nitinol, polymer, or plastic. As with the embodiment described above, the collapsible box system can be configured to detach for permanent implantation or can be used to retain distraction of the joint 36 while an auxiliary implant or gel is positioned in the distracted joint 36.

In use, the collapsible box can be inserted through the cannula of an access system as described previously to position the collapsible box within the facet joint 36. The box can be actuated with the handle 67 of the tool causing the box to transition from a collapsed or flat parallelogram configuration to an expanded rectangular configuration. As is probably best appreciated by reference to FIG. 7A, the collapsible box can be moved between its collapsed and expanded conditions by actuating the handle 67, which can pull or push on an upper flexible but somewhat rigid strip 72 connected to the upper wall 64 while a lower similar strip 74 connected to the lower wall 66 holds the lower wall 66 in a fixed position. The expansion can create separation of the facet joint 36 in both the vertical and horizontal planes. As the collapsible box expands and causes distraction and translation, the fixation mechanisms 70 engage the facet surfaces securing the structure and allowing for controlled distraction and translation of the facet joint 36.

Figure 8A:
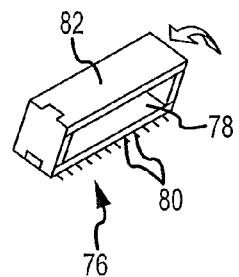
FIG. 8A is an isometric of an expandable tip of a distraction device showing a third embodiment of the present invention.
Figure 8B:
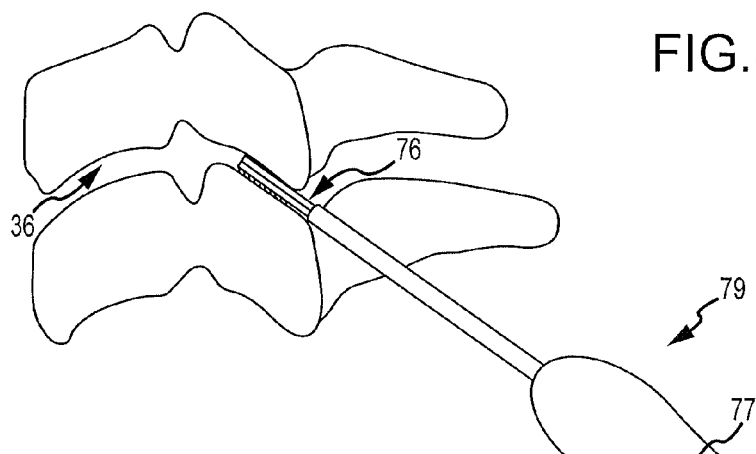
FIG. 8B is a side elevation showing the device of FIG. 8A positioned on the distal end of a distraction tool with the device inserted into a facet joint.
Figure 8C:
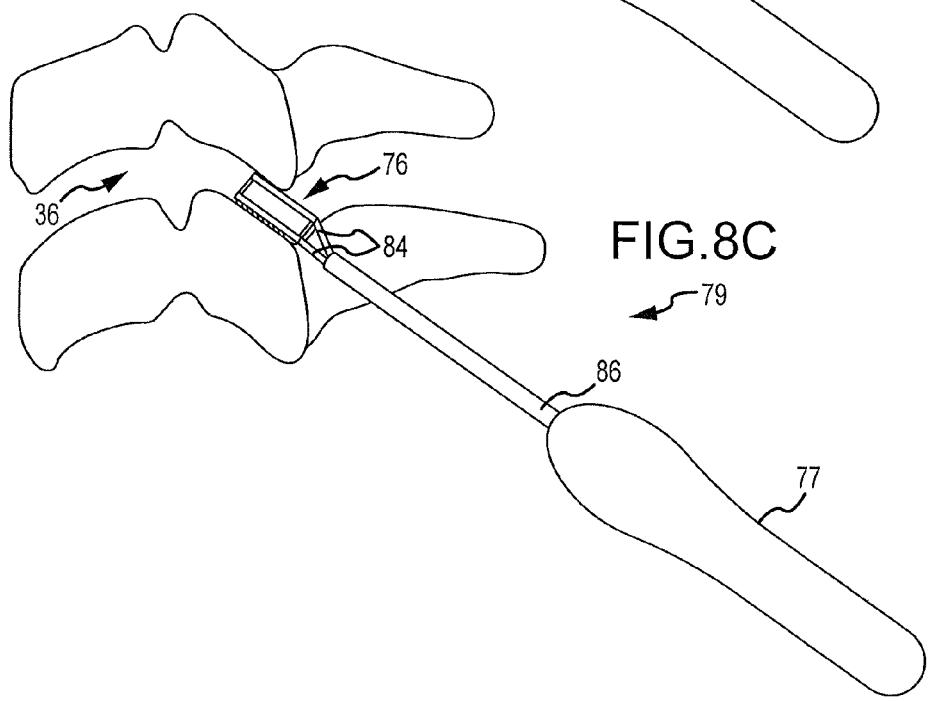
FIG. 8C is a side elevation similar to FIG. 8B with the device expanded to distract the facet joint.

A third embodiment of a delivery tool 79 in accordance with the invention is shown in FIGS. 8A-8C and can be seen to be similar to that of the second embodiment of FIGS. 7A-7C. In this embodiment, a distraction mechanism 76 in the form of a collapsible box is again utilized but the bottom surface of the lower wall 78 of the box has fixation mechanisms 80 for engaging the lower facet to hold the lower wall 78 of the box in a fixed position while the upper wall of the box with no such teeth is shifted relative thereto with a pair of rigid but somewhat flexible strips 84 that can be extended or retracted with the insertion handle 77 to expand or flatten the collapsible box, respectively.

Figure 9A:
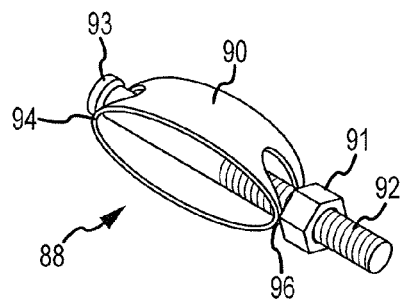
FIG. 9A is a fragmentary isometric of the distal tip of a distraction device showing a fourth embodiment of the present invention.
Figure 9B:
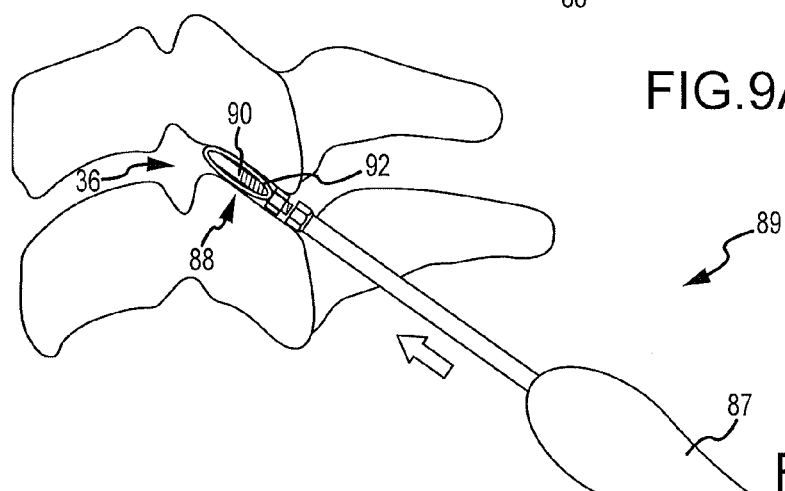
FIG. 9B is a side elevation showing the device of FIG. 9A positioned in a facet joint.
Figure 9C:
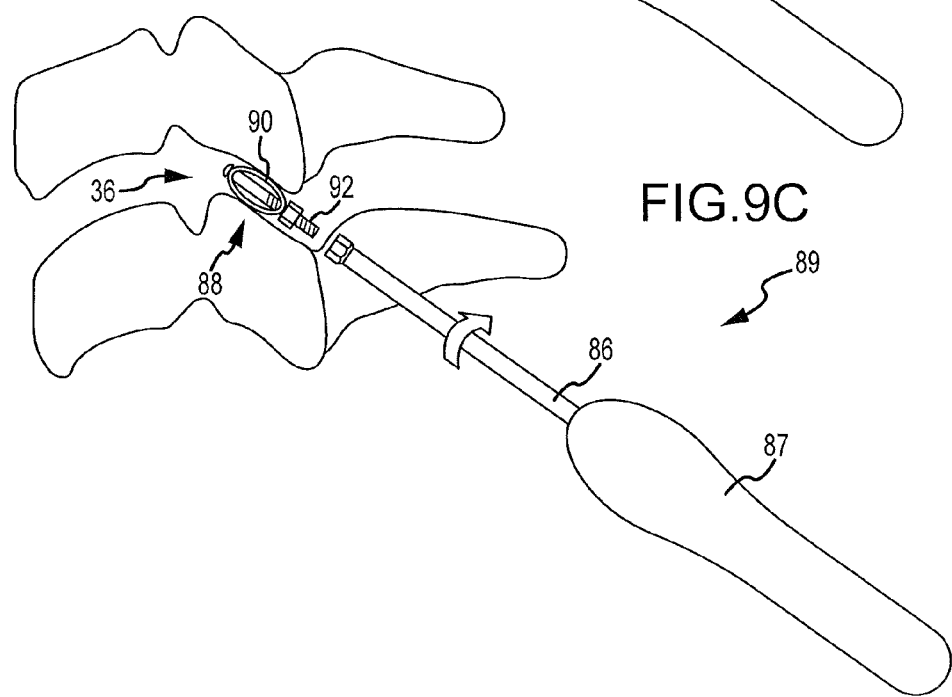
FIG. 9C is a side elevation similar to FIG. 9B with the device expanded.

A fourth embodiment of a delivery tool 89 in accordance with the present invention is shown in FIGS. 9A-9C. In this embodiment of the invention, the distraction mechanism 88 can have a diamond-shaped or oblong distraction head 90 made from a somewhat rigid but flexible band or strip of material. The mechanism 88 can include an actuator in the form of an elongate member 92 extending longitudinally there through that is adapted to draw the opposing ends 94, 96 of the distraction head 90 together. The elongate member 92 can be a threaded member adapted to draw the ends 94, 96 of the head 90 together by interaction with a female member 91. The interaction can be via a screw action with a female threaded member as shown. Alternatively, the elongate member 92 can be a toothed member adapted to draw the ends 94, 96 of the head 90 together via a ratcheting action with a female ratchet member similar to that of a cable tie. In either case, the elongate member 92 can extend through the head 90 of the distraction mechanism 88 and can include a stop or flange 93 on a distal end preventing the head 90 from advancing beyond the distal end of the elongate member 92. The female member 91 can be positioned on the elongate member 92 just proximal to the head 90. Advancing the female member 91 along the elongate member 92 via screwing action or sliding ratcheting action can compress the head 90 between the female member 91 and the flange 93 thereby causing the head 90 to expand as shown when comparing FIG. 9B to 9C.

It is noted that several alternative configurations and relationships of the elongate member 92 with a female member 91 can be provided. That is, for example, one end of the head 90 can form the female member 91 such that actuation of the elongate member 92 causes the end of the head 90 with the female member 91 to walk along the elongate member 92 thereby drawing the ends 94, 96 of the head together. Other configurations and relationships can be provided and are within the scope of the present invention.

It is also noted that FIGS. 9A-9C depict a female member 91 in the form of a nut that is threadable over an elongate member 92 in the form of a bolt. Accordingly, the cannula 86 of the delivery tool 89 includes a distal tip in the form of a nut driver. Those of skill in the art will understand and appreciate that alternative engagements between the cannula 86 and the female member 91 or the elongate member 92 can be provided. That is, depending on the configuration, actuation may required that the female member 91 be rotated or advanced and in other configurations, the elongate member 92 may need to be rotated, advanced, or even withdrawn. In some embodiments, the engagement between the cannula 86 and the female member 91 or elongate member 92 can be, for example, a straight screw driver tip, an allen wrench type tip, or other engaging shapes.

The head 90 of the distraction mechanism 88 can be made out of titanium, steel, carbon, PEEK, nitinol, or plastic. Other materials can be used. The distraction mechanism 88 can be configured to detach from the delivery tool 89 as shown so that it becomes a permanent implant. Alternatively, the distraction mechanism 88 can be used only for distraction purposes so that a separate implant can be positioned in the facet joint 36 to retain the distraction while the distraction mechanism 88 is removed. In this embodiment, the cannula 86 can include a more permanent connection to the female member 91 or elongate member 92 in contrast to that depicted in FIGS. 7B and 7C.

In use, energy can be applied to the flattened diamond or oblong head 90 via the handle 87 and cannula 86 assembly. The energy can cause the opposing ends 94, 96 of the head 90 to draw together and the head 90 can expand resulting in an increased height in the head 90. The expansion of the head 90 can cause the surfaces of the head 90 to engage with the facet surfaces. As the head 90 expands against the facet surfaces, the joint 36 can separate in both the horizontal and vertical planes. This separation can lead to distraction and forward translation of the facet joint 36. Moreover, the flexible nature of the head 90, while sufficiently rigid to cause separation of the joint 36, may also conform to the contour of the articular surfaces of the facet joint 36 thereby distributing the compressive load from the joint 36 more evenly over the surface interacting with the distraction mechanism 88. This shape conformance can also function to resists withdrawal or dislodgement of the implant. Additionally, while not shown, the head 90 of the device can include fixation mechanisms along the surface of the head 90 adapted to engage the articular surfaces of the facet joint 36.

Figure 10A:
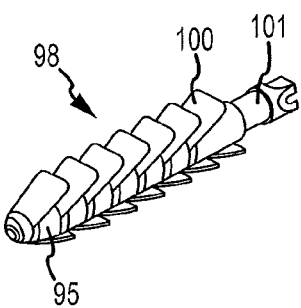
FIG. 10A is an isometric of a fifth embodiment of the device of the present invention.
Figure 10B:
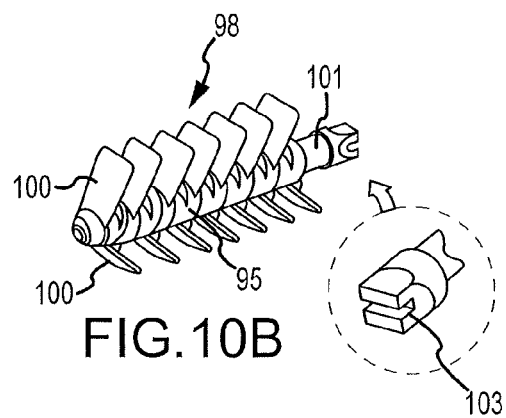
FIG. 10B is an isometric similar to FIG. 10A with the device expanded.
Figure 10C:
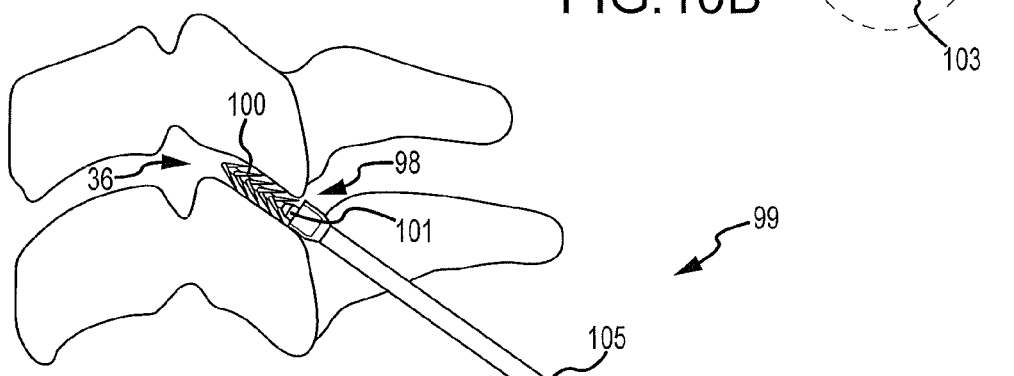
FIG. 10C is a side view showing the device of FIG. 10A positioned on the distal end of a distraction tool.
Figure 10D:
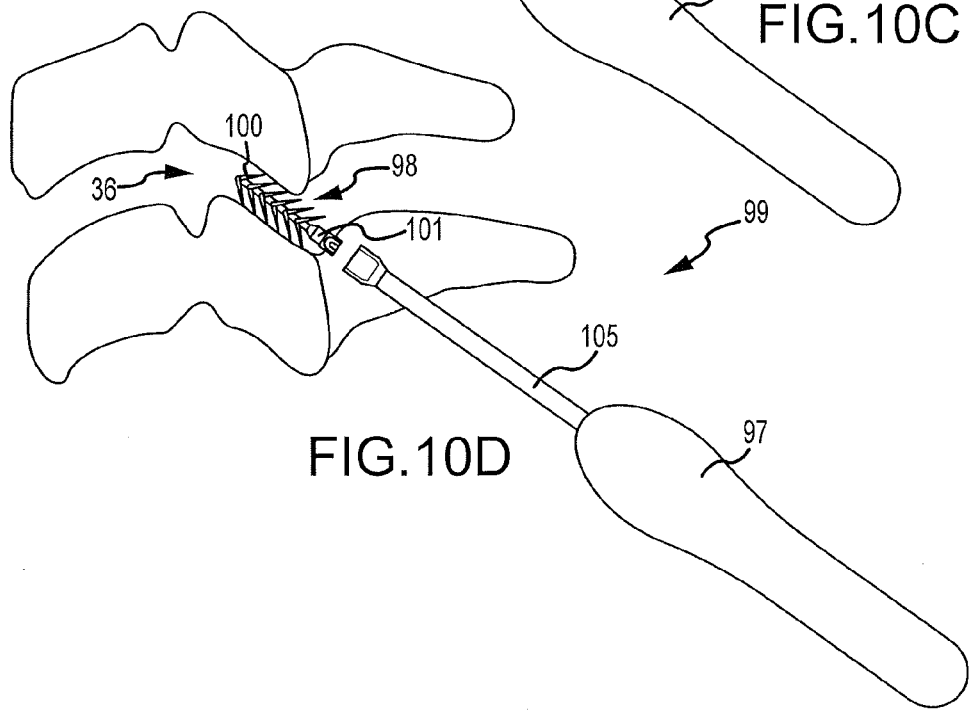
FIG. 10D is a side view similar to FIG. 10C with the device expanded as in FIG. 10B and separated from the insertion tool.

A fifth embodiment of the distraction mechanism of the present invention is shown in FIGS. 10A-10D. In this embodiment, pairs of pivotal teeth 100 can be mounted on a common base or central core 95. The teeth 100 can be pivotal between a folded or retracted position as shown in FIG. 10C or the teeth 100 can be pivoted outwardly. Each pair of teeth 100 may be pivotal independent of the other teeth 100. However, as in the embodiment shown, the teeth 100 may overlap in the retracted position such that when underlying teeth 100 are pivoted outwardly the overlying teeth 100 are naturally lifted. The retracted position can provide for insertion of the mechanism 98 into a facet joint 36 and the outwardly pivoted position can serve to distract the joint 36.

The distraction mechanism 98 can also include an actuation device in the form of an elongate member 101 adapted to be advanced into the base or central core, where advancing the elongate member 101 can serve to actuate the teeth 100 and pivot them outwardly. As shown, the elongate member 101 can be a threaded member and the central core 95 can include thread slots positioned below the position of the retracted teeth 100 and relatively close to the pivot point of the teeth 100. Accordingly, when threaded member is advanced into central core 95, the threads from the threaded member can protrude through the thread slots and can engage the teeth 100 relatively close to the pivot point of the teeth 100. The protruding thread can thus distract the teeth 100 and pivot them outward. As the threaded member is continually advanced, additional teeth 100 can be distracted thereby distracting the facet joint 36. The close proximity of the protruding thread to the pivot point of the teeth 100 can function to minimize the distance that the thread must protrude to suitably distract the associated teeth 100.

In an alternative embodiment, the elongate member 101 may be a longitudinal shaft with radiused fins positioned along two lateral sides of the shaft. Each pair of fins can be positioned to correspond to each pair of teeth 100 and the fins can be positioned longitudinally along the elongate member 101 so as to be in close proximity to the pivot point of a respective pair of teeth 100. The elongate member 101 can be rotated causing the fins to pass beneath the teeth 100 near their respective pivot points and cause the teeth 100 to simultaneously pivot outward.

In still another embodiment, the elongate member 101 can be in the form of plunger type actuation device. In this embodiment, the teeth 100 may extend through the base or central core 95 via a slit in the base or central core 95. The teeth 100 can further extend to and be pivotally connected to the elongate member 101 passing through the central core 95. Accordingly, advancing the elongate member 101 forward or distally can cause the teeth 100 to retract due to decreasing the angle of the pivot point of the elongate member 101 relative to the slit through which it passes. Withdrawing the elongate member 101, on the other hand, can cause the teeth 100 to pivot outwardly simultaneously thus functioning to distract the joint 36. In this embodiment, the elongate member 101 can threadably engage the inside of the central core 95 to allow for controlled advancement and withdrawal of the elongate member 101 or the elongate member 101 can be slidably received in the central core 95.

Any or all of the above described elongate members 101 can include an engagement feature at a proximal end for engagement by the cannula 105 or device positioned within the cannula 105. The engagement feature can be adapted to provide for transferring rotational, advancing, or withdrawing forces. As shown, the engagement feature can include a straight screw driver receiving slot 103. The engagement feature can be an allen type connection or a hex head for receiving a nut driving device, or a square head for receiving a square drive device. Those of skill in the art will understand and appreciate that several engagement features are available and are within the scope of the invention.

When energy is applied to the handle 97 of the tool 99, the teeth 100 of each pair can change their orientation or expand to achieve a suitable angle relative to the central core 95. In some embodiments this angle can range from approximately 10° to approximately 90°. In other embodiments, this angle can be approximately 45°. In this embodiment, in its fully expanded state, the mechanism 98 can take on the appearance of a Christmas tree.

In use, the mechanism 98 can be inserted into the facet joint 36 in a flattened, collapsed state. Distraction energy can be applied to the handle 97 causing the mechanism 98 to expand which causes the multiple teeth 100 to engage both the top and bottom facet surfaces of the joint 36. As the mechanism 98 is expanded to achieve increasingly larger dimensions, the facet joint 36 surfaces can separate. This separation in both the vertical and horizontal planes of the facet joint 36 can cause distraction and translation of the facet joint 36.

Figure 11A:
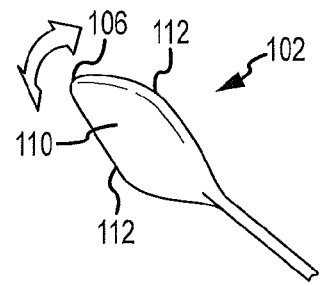
FIG. 11A is a fragmentary isometric of a sixth embodiment of the present invention.
Figure 11B:
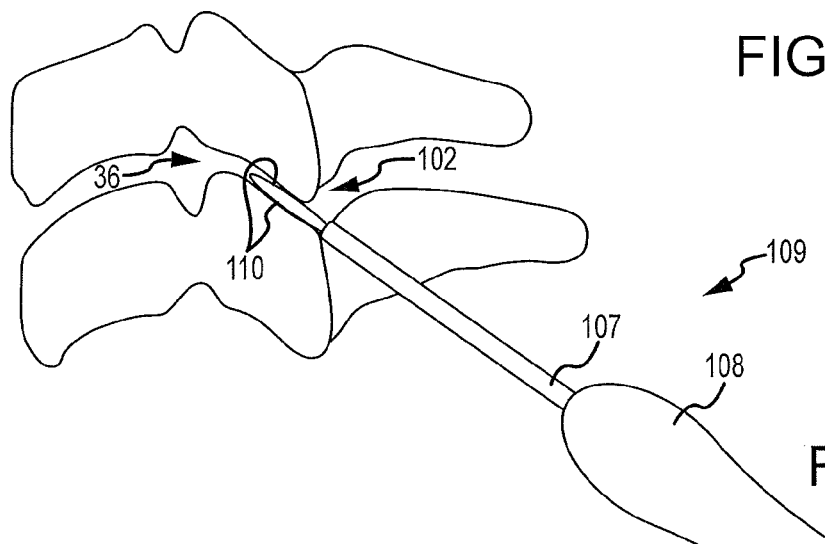
FIG. 11B is a side view showing the device of FIG. 11A inserted into a facet joint.
Figure 11C:
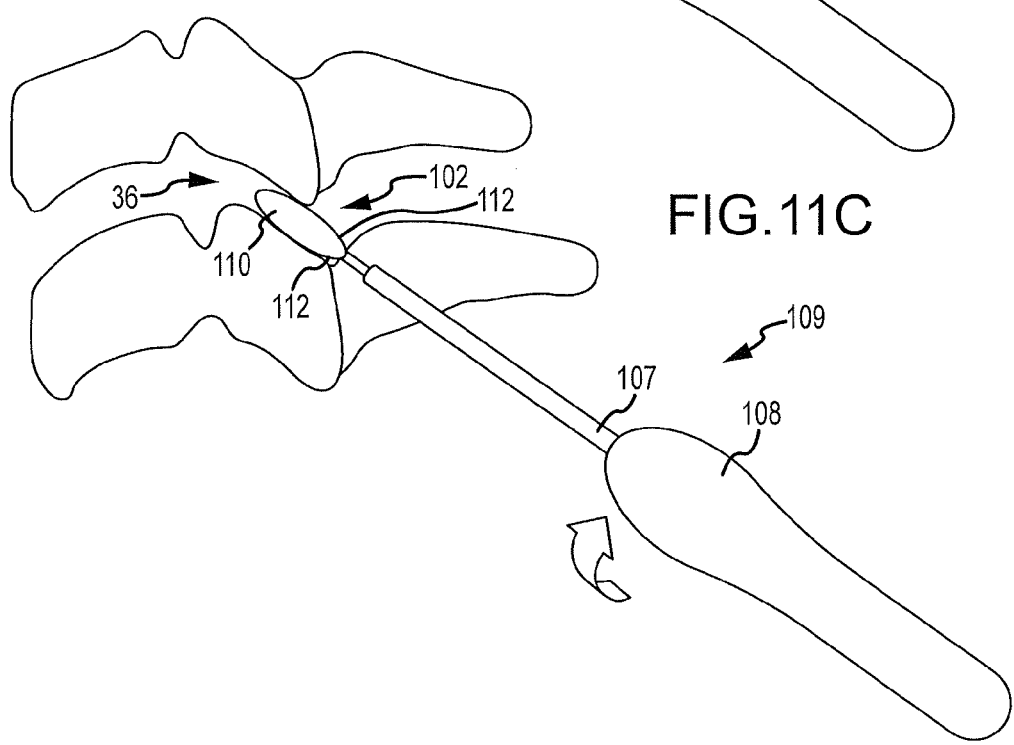
FIG. 11C is a side view similar to FIG. 11B with the device having been rotated with the insertion tool to distract the facet joint.
Figure 12A:
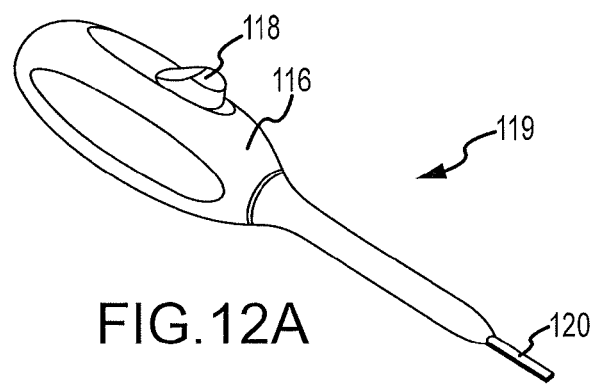
FIG. 12A is an isometric of the handle of a seventh embodiment of the present invention.
Figure 12B:
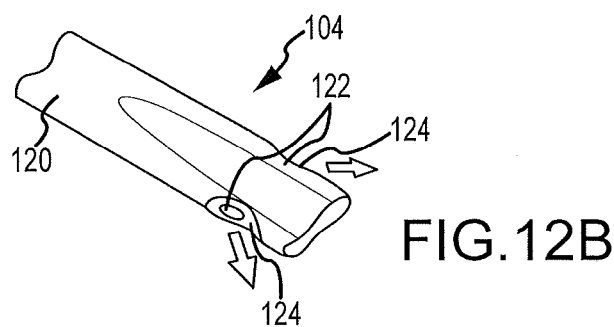
FIG. 12B is the distal tip of the seventh embodiment of the handle which is shown in FIG. 12A.
Figure 12C:
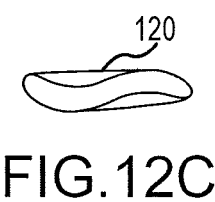
FIG. 12C is a transverse section of the distal tip as shown in FIG. 12B.
Figure 12D:
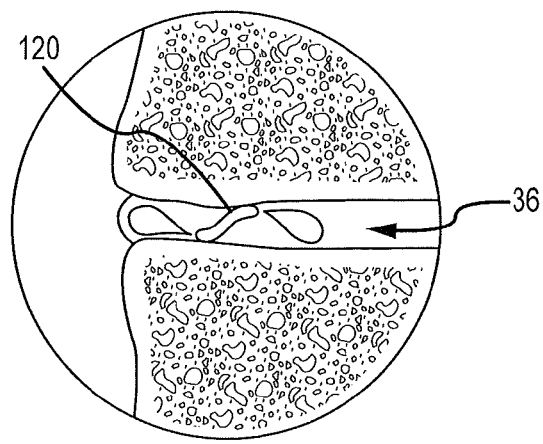
FIG. 12D is a diagrammatic cross-section through a facet joint with the device of FIG. 12B positioned therein and having injected a gel substance into the facet joint.

A sixth embodiment of a tool 109 of the present invention is shown in FIGS. 11A-11C. In this embodiment, the distraction mechanism 102 at the distal end of the tool 109 can have a relatively flat and ovular head 110 with a beveled tip 106 to facilitate insertion into the facet joint 36. The mechanism 102 can have opposing relatively flat surfaces where the edges 112 interconnecting the surfaces are rounded along the lateral and medial edges of the mechanism 102. The distraction mechanism 102 can be connected to the distal end of the cannula 107 with a rotationally resistive connection such that rotation of the cannula 107 causes rotation of the mechanism 102.

In use, distraction energy can be applied to the handle 108 of the deliver tool 109 to cause rotation of the distraction mechanism 102. As the flat head 110 of the mechanism 102 rotates, the articular surfaces of the facets can be forced apart due to a height of the mechanism (through the width of the head 110) being greater than its flattened dimension. The increased height achieved from rotation of the mechanism 102 can cause the flat, round surfaces of the mechanism 102 to engage the facet surfaces and separate them. This rotational distraction can result in vertical and horizontal separation of the facet joints 36 achieving distraction and forward translation of the joint 36.

The distraction mechanism 102 can be mounted on the distal end of the delivery tool 109 so that it can be removed from the delivery tool 109 if desired to remain as an implant to retain the distraction of the joint 36 or can be retained in position until an auxiliary implant is positioned in the joint 36 and then removed with the delivery tool 109.

A seventh embodiment of the present invention is shown in FIGS. 12A-12D. This embodiment is similar to that of the sixth embodiment in that the mechanism 104 is rotatable to achieve distraction of the joint 36, but rather than possibly serving as a mechanical implant, as is possible with the sixth embodiment, the mechanism 104 can be used to inject a fluid such as a hydrogel, PMMA bone cement, BMP, silicone, or the like, into the facet joint 36. The distraction mechanism 104 can be mounted on the distal end of a delivery tool 114, which uses a thumb slide 118 for applying energy to the mechanism 104. The distraction mechanism 104 comprises a somewhat flattened and rigid blade 120 that is slightly S-shaped in cross-section and is hollow with the hollow interior of the mechanism 104 communicating with lateral ports 122 in notches 124 formed in the side edges of the blade 120. When the mechanism 104 is inserted into a facet joint 36, it is inserted with its relative flat dimension oriented generally parallel to the articular surfaces of the joint 36. To obtain distraction, the mechanism 104 can be rotated with the delivery tool 119, which can cause the joint 36 to distract. Once the joint 36 has been distracted, a gel or other suitable fluid can be emitted through manipulation of the thumb slide 118 on the delivery tool 119 so that the gel is forced through the hollow interior of the device and out the injection ports 122 to fill the facet joint 36 to the desired level. The distraction mechanism 104 can then be withdrawn with the gel serving as an implant to retain the distracted joint 36 at the desired separation.

As with the rest of the embodiments of the invention described herein, in some versions of the embodiment depicted in FIGS. 12A-12D, the tool 119 may include a central delivery lumen through which an implant may be delivered, for example, via a plunger or push rod, to the distracted facet or joint space. In other versions of the embodiment depicted in FIGS. 12A-12D, another delivery tool may be employed once the distraction mechanism 104 has distracted the joint 36.

Figure 13A:
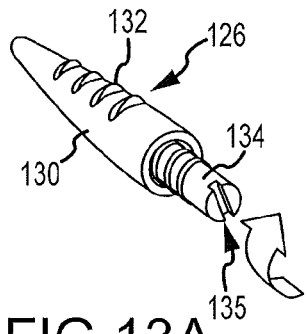
FIGS. 13A and 13B are fragmentary isometric views of a tip of a distraction device in accordance with the present invention showing an eighth embodiment of the distal tip of the device.
Figure 13B:
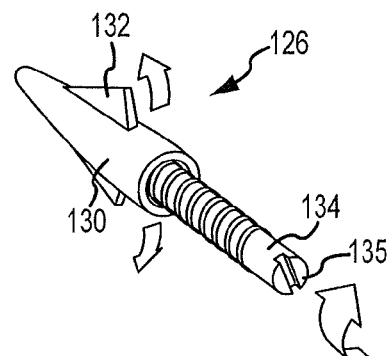
Figure 13C:
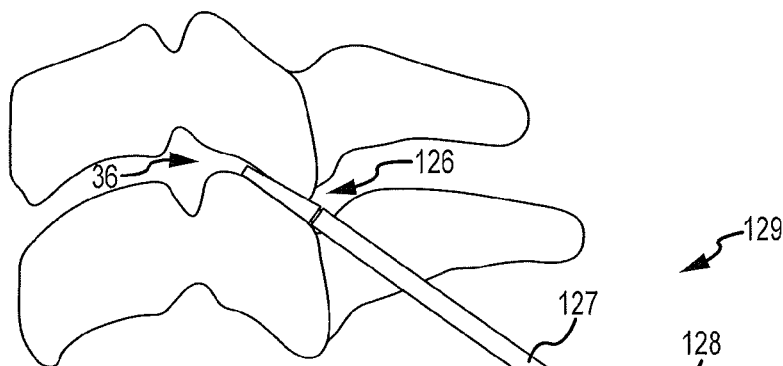
FIG. 13C is a side view of a tool inserting the device of FIG. 13A into a facet joint.
Figure 13D:
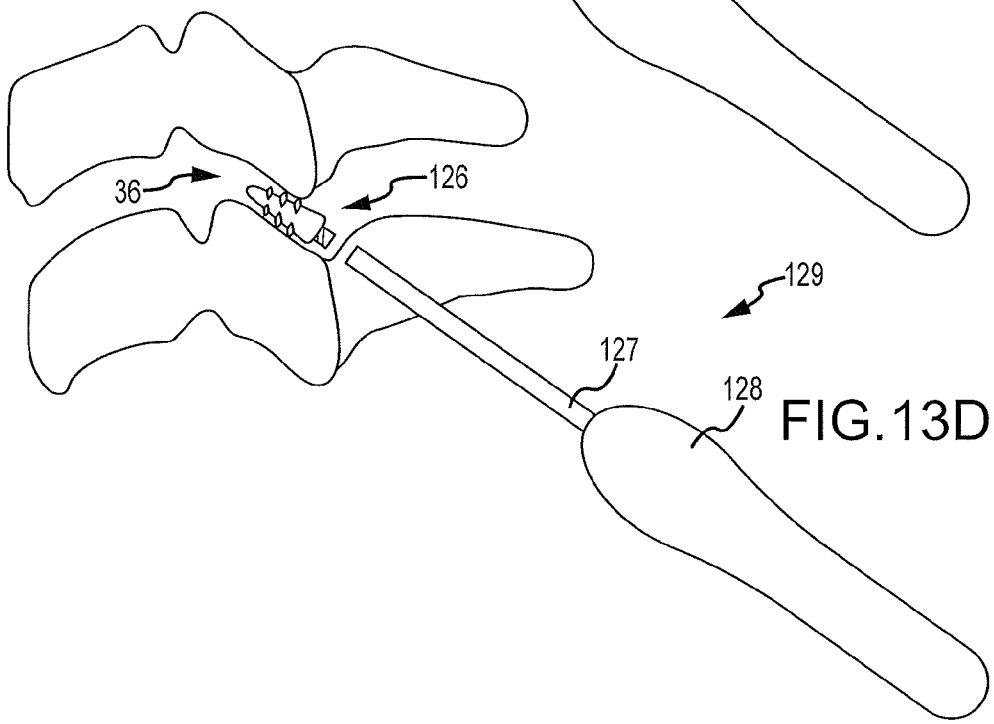
FIG. 13D is a side view similar to FIG. 13C with the device of FIG. 13A having been rotated to distract the facet joint and the insertion device removed from the tip which serves as an implant.
Figure 13E:
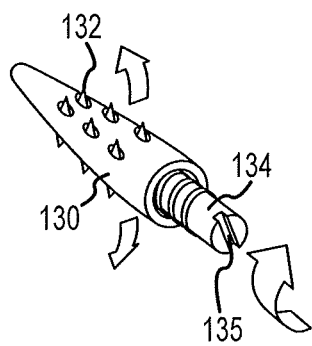
FIGS. 13E-13H are respectively the same views as depicted in FIGS. 13A-13D, except of a variation of the embodiment depicted in FIGS. 13A-13D.
Figure 13F:
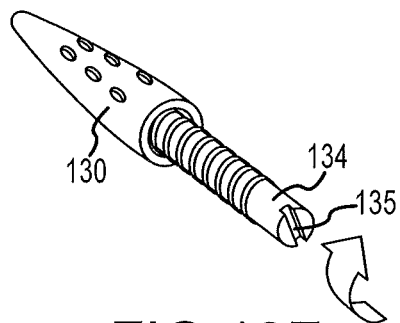
Figure 13G:
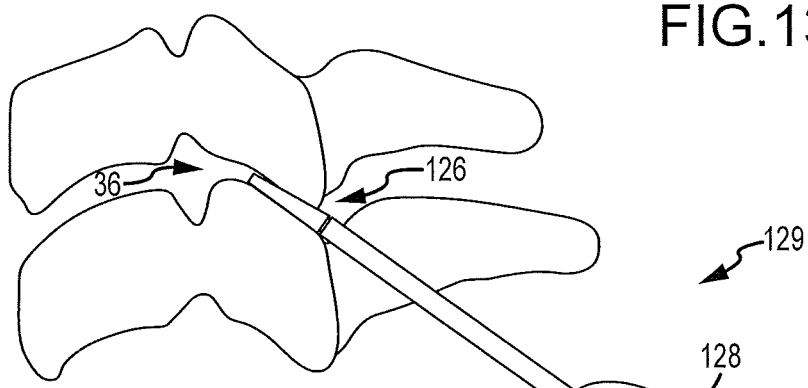
Figure 13H:
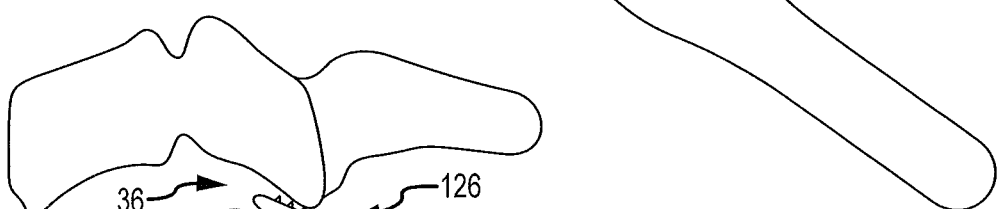

An eighth embodiment of the invention is shown in FIGS. 13A-13D. In this embodiment, the distraction mechanism 126 can have a generally hollow elongated body 130. In some embodiments, the body 130 may be relatively cone-shaped. The thickness of the body 130 can be small enough so it can be initially inserted a short distance into a relatively flat and collapsed facet joint 36. The body 130 can include facet engaging features 132 including diametrically opposed deployable keels (FIG. 13B), thread slots (FIGS. 13A and 13D), or deployable teeth (FIGS. 13E, 13F, and 13H). The keels can have a retracted position wherein they lie within the confines of the body 130, but, when activated as indicated with the arrows in FIG. 13B, extend in a tapered manner away from the outer surface of the body 130. The thread slots shown in FIG. 13A can be adapted to receive treads from an actuator that can be advanced through the body 130 to distract the facet joint 36. The threads of the actuator can gain purchase in the articular surfaces of the facet by protruding through the thread slots of the body 130. The deployable teeth, like the keels, can have a retracted position wherein they lie within the confines of the body 130, but, when activated, extend through openings in the body 130 to engage the articular surfaces of the facet joint.

The distraction mechanism 126 can include an actuator as shown in the form of an elongate member 134. The elongate member 134 can be a threaded member or a toothed ratchet type member adapted to be inserted through the hollow core of the body 130. As shown in FIGS. 13A and 13B, the elongate member 134 can be a screw or bolt type member adapted to threadably engage the body 130. The elongate member 134 can be actuated and advanced via distraction energy applied to the tool 129 via a handle 128 as previously described. In the case of a body 130 having keels, the advancing elongate member 134 can result in the expanding keels engaging the facet surfaces of the joint 36 causing separation of the joint 36 as increasingly more distraction energy is applied resulting in progressively more deployment and height of the device with the keels also providing fixation to the facet surfaces. In the case of threaded slots, the advancement of the elongate member 134 can expand or stretch the body 130 or merely advance through the body 130. As the threads of the elongate member 134 engage the threaded slots, the threads can protrude through the slots and cut into or otherwise engage the articular surfaces of the facet joint 36. In the case of deployable teeth, the advancing elongate member 134 can force the teeth through openings in the body 130 thereby causing them to engage the facet surfaces of the joint 36 allowing for secured positioning of the implant.

As shown, the elongate member 134 can include an engagement feature 135 for receiving a corresponding engagement feature from the cannula 127 of the delivery tool. As shown the engagement feature 135 of the elongate member can be adapted to receive a straight screw driver tip. Other rotating and/or driving engagements can be provided.

Figure 14A:
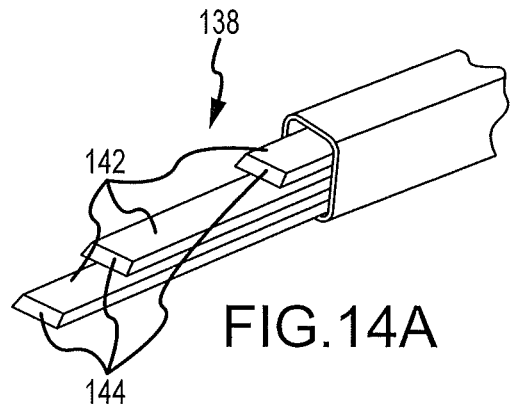
FIG. 14A is an isometric showing the tip of a ninth embodiment of a distraction device in accordance with the present invention.
Figure 14B:
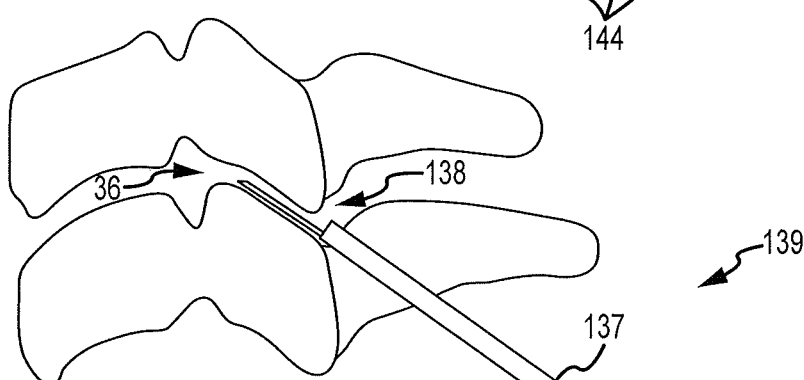
FIG. 14B is a side view showing the distraction device of FIG. 14A inserted into a facet joint with an insertion tool.
Figure 14C:
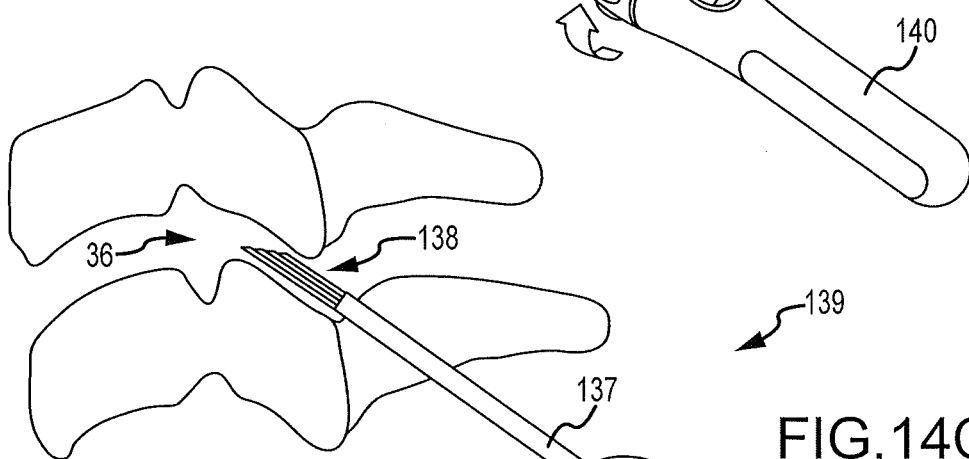
FIG. 14C is a side view similar to FIG. 14B with a plurality of blades or spatula elements having been advanced into the facet joint to distract the joint.

A ninth embodiment of the invention is shown in FIGS. 14A-14C. In this embodiment, the distraction mechanism 138 may include one or more leaf blades 142 with tapered tips 144. The blades 142 may extend longitudinally from a delivery tool cannula 137 and may be stacked relative to one another. The blades 142 may be actuatable independent of one another and may be actuatable in consecutive order.

The blades 142 can be made of steel, titanium, PEEK, carbon, or nitinol. Other materials can be used. The blades 142 can be configured as temporary distraction shims or permanent detachable implants which can be left in the distracted joint 36. If the stacked blades 142 are configured for detachment and permanent implantation, they can include one or more of the previously described fixation mechanisms. Additionally, the blades 142 can include relative motion restraints adapted to prevent relative slippage from occurring between blades 142. These restraints can include detent recesses and protrusions or other restraints.

The distraction achieved with this system can occur by advancing the blades 142 one at a time into the facet joint 36 so that as an increasing thickness or height of the stack of blades 142 is inserted into the joint 36, distraction is achieved. The number of blades 142 extended into the joint 36 can be increased until the desired distraction of the joint 36 is achieved.

The handle 140 of the present embodiment can include any of the handles previously described. However, as shown in FIGS. 14B and 14C, the handle 140 can include a rotating dial type handle 140 such that rotation of the dial relative to the handle 140 causes actuation of the blades 142. This can occur through an internal screw system that can convert radial motion to longitudinal motion. Additionally, the proximal ends of the blades can be initially staggered such that an internally advancing rod can first engage and advance the bottom blade, and then the next blade, and the next blade, and so on. Accommodations can also be made to avoid continued advancement of a given blade 142 once it enters the joint. Accordingly, incremental rotation of the dial can cause incremental advancement of the internal rod and thus consecutive advancement of blades 142.

The dial can include measurements corresponding to the thickness of each of the advancing blades 142 and can thus display to the user, the total distraction being provided by the blades 142. That is, rotation of the dial can advance a first blade 142 into the joint 36 and the indication on the dial can reflect the thickness of the first blade 142 and thus the resulting distraction. Upon further rotation of the dial, additional blades 142 can be advanced into the joint 36 and the indication on the dial can reflect the cumulative thickness of the first blade 142 and the additional blades thereby reflecting the total distraction.

Accordingly, the present embodiment can be used to distract a facet joint 36 as described and can also be used as an implant. However, the tool 139 can also be used to calibrate or prepare for a distraction procedure by assisting a user in determining the appropriate amount of distraction. In one embodiment, the tool 139 described can be used to obtain intra operative feedback from a patient. The tool 139 can be use to incrementally distract a joint 36 to determine how much distraction is necessary to alleviate patient symptoms. Based on feedback from the patient, an appropriately sized implant can be selected for insertion into the facet joint 36. The current embodiment can then be used to maintain the facet joint 36 in a distracted condition for placement of the implant or other devices can be used to place the implant.

In one version of the embodiment depicted in FIGS. 14A-14C, each of the blades 142 of the mechanism 138 may have a longitudinally extending slot (not shown) defined therein and positionally corresponding with the slots of the adjacent blades 142 to define an overall slot (not shown) through which an implant may be delivered, for example, via a plunger or push rod, to the distracted facet or joint 36 space. In other versions of the embodiment depicted in FIGS. 14A-14C, another delivery device may be employed once the mechanism 138 is used to distract the facet joint 36.

Figure 15A:
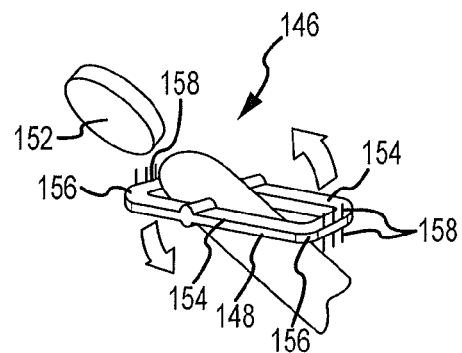
FIG. 15A is an isometric of a tenth embodiment of a distraction device in accordance with the present invention.
Figure 15B:
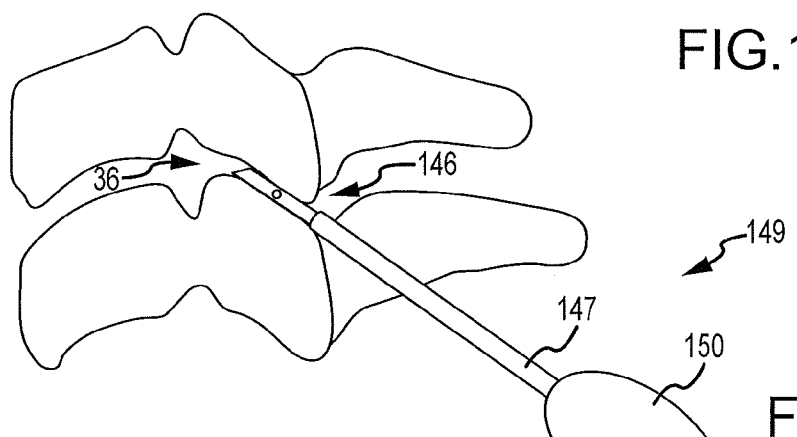
FIG. 15B is a side view of the device shown in FIG. 15A on the distal end of an insertion tool and positioned within a facet joint.
Figure 15C:
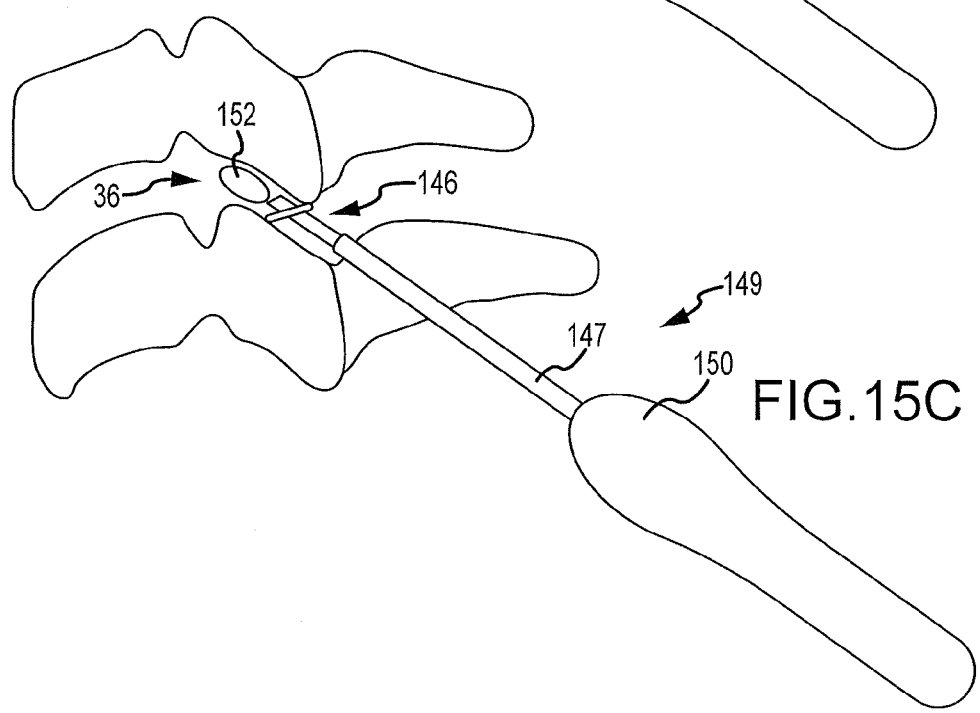
FIG. 15C is a side view similar to FIG. 15B with the distraction device having been expanded to distract the facet joint and deliver a permanent implant into the distracted joint.

Referring to FIGS. 15A-15C, a tenth embodiment of a distraction mechanism 146 of the invention is illustrated. In this embodiment, a rotatable loop 148 of rectangular configuration made of a rigid material can be pivotally mounted on the distal end of the delivery tool 149 and can carry within the loop 148 an implant of the type disclosed in the prior embodiments, or of types to be disclosed hereafter, which can be deposited or left in a distracted joint 36. The loop 1478 can have elongated side legs 154 and relatively short end legs 156 with fixation mechanisms 158 such as teeth on both surfaces of the short legs 156 of the loop 148. The pivotal mount between the loop 148 and the deliver tool 149 can be positioned approximately midway along the length of the side legs 154.

Distraction energy can be applied to the rigid loop 148 from the handle end of the delivery tool 149 causing the trailing end of the loop 148 to rotate forwardly, as illustrated with the arrows in FIG. 15A (posterior to anterior). Together with the teeth on the surface of the loop 148, the loop 148 can engage the facet surfaces to separate the joint 36. The forward rotation of the loop 148 can distract the joint 36 and also push the superior facet slightly forward in translation relative to the inferior facet.

When the desired distraction and translation of the facet joint 36 is achieved, the tool 149 can deposit the implant, which is carried within the loop 148. The implant can be carried within a hollow inside the cannula 147, for example. The implant can be introduced into the distracted joint 36 and deposited therein prior to the mechanism 146 being removed.

Figure 16A:
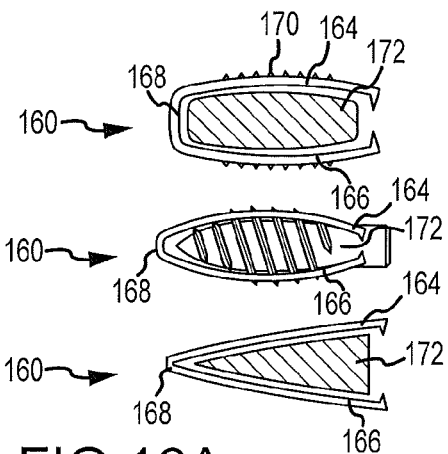
FIG. 16A is a side view of an eleventh embodiment of a distraction device in accordance with the present invention, showing a wedge option, an elongated member option, and a block option.
Figure 16B:
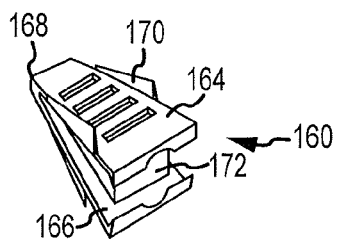
FIG. 16B is an isometric of the wedge option of FIG. 16A.
Figure 16C:
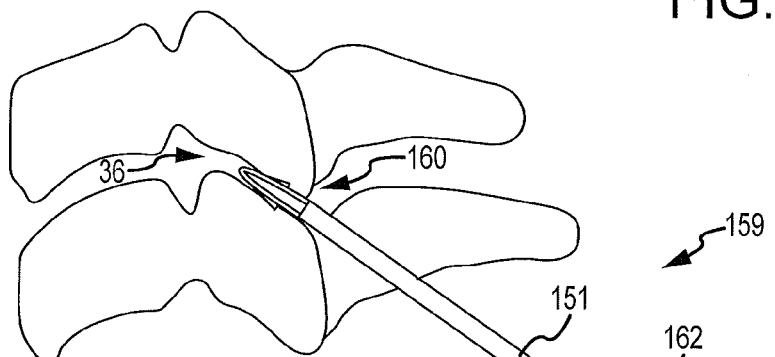
FIG. 16C is a side view of the distraction device of FIG. 16A positioned within a facet joint on the distal tip of an insertion tool.
Figure 16D:
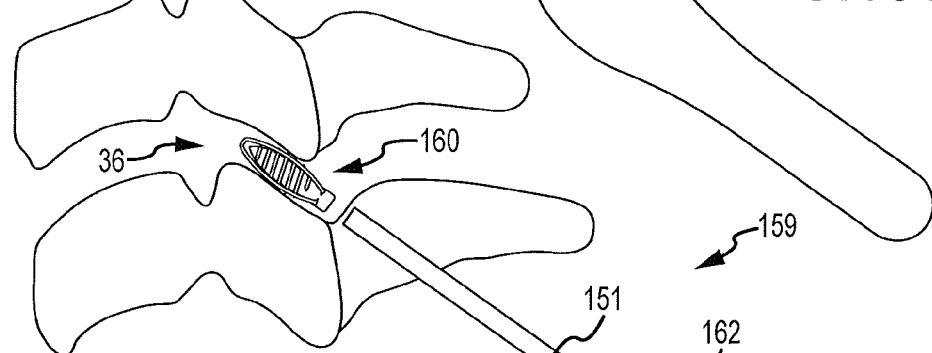
FIG. 16D is a side view similar to FIG. 16B with the distraction device expanded to distract the facet joint and with the insertion tool having been separated therefrom.

An eleventh embodiment of a distraction mechanism 160 of the present invention is shown in FIGS. 16A-16C. The distraction mechanism 160 can include an expandable receiving portion having upper 164 and lower 166 generally planar elements which are connected at an end with a living hinge so that the mechanism 160 can be flattened for insertion into a facet joint 36. As shown, the upper and lower generally planar elements 164, 166 can be relatively triangularly shaped or trapezoidally shaped with the living hinge being positioned near the narrower end of the respective shapes. Other shapes, such as, for example, rectangular, of the planar elements 164, 166 can be used. The outer surface of the planar elements 164, 166 can include tapered keels as fixation mechanisms 170 which assist in gripping the superior and inferior facet surfaces. The keels can be provided along the edges of the planar surfaces 164, 166 as shown or they can be provided more centrally to the planar surfaces 164, 166. The outer surface can also include threaded slots as fixation mechanisms 170 for receiving threads from an actuator being advanced into the receiving portion. The outer surface can also include teeth as fixation mechanisms 170 adapted to engage the facet surfaces.

An actuation device 172 can be included, as shown in FIG. 16A, and can take the form of a wedge, an elongated member, or block-type member. In the case of a wedge actuation device, the wedge can be advanced into the receiving portion between the planar members 164, 166 forcing the planar members 164, 166 apart and distracting the joint 36, as shown in FIG. 16B. The fixation mechanisms 170 on the surface of the planar members 164, 166 can engage the facet surfaces thereby resisting any tendency for the mechanism 160 to back out of the joint 36.

In the case of an elongate member, the elongate member can be advanced between the planar members 164, 166 forcing the planar members 164, 166 apart and distracting the joint 36. As shown, the elongate member may include a tapered tip to initiate the advancement. In addition, the elongate member can include threads to facilitate advancement into the receiving portion. Moreover, where threaded slots are provided on the planar members 164, 166, the threads of the elongate member can engage the threaded slots and protrude through the threaded slots. Accordingly, the threads can cut into or otherwise gain purchase in the facet surfaces to prevent any back out tendency of the mechanism 160.

In the case of a block-type actuation device, the block can be advanced between the planar members 164, 166 forcing the planar members 164, 166 apart and distracting the joint 36. The block can include a taper (not shown) at a distal end for initially engaging and separating the planar members 164, 166. Alternatively or additionally, a portion of the planar members 164, 166 may extend outside the facet joint 36 and may be pried apart for initial insertion of the block after which the forced advancement of the block can cause separation of the facet allowing the block to be fully inserted into the receiving portion and into the facet joint 36. Where the receiving portion includes teeth and/or keels, these fixation mechanisms 170 can be forced into the facet surfaces gaining purchase therein.

The receiving portion of the mechanism 160 can be carried on the distal end of a delivery tool 159 and can be inserted into the facet joint 36 in a collapsed state. One of the actuation devices 172 described can then be inserted into the receiving portion from its open trailing end to expand the receiving portion by separating the planar elements 164, 166 until the desired distraction of the joint 36 is achieved. This separation can lead to distraction and forward translation of the facet joint 36.

As shown in FIGS. 16A and 16B, the receiving portion can conform to the shape of the articular surfaces of the facet joint 36 as described with respect to the embodiment shown in FIG. 9. As such, the distraction mechanism 160 can distribute the compressive load from the joint 36 more evenly over the surface interacting with the distraction mechanism 160. This shape conformance can also function to resists withdrawal or dislodgement of the mechanism 160 or implant. It is further noted that this shape conformance can be multidirectional and where the keels are positioned along the edges of the planar elements 164, 166, the keels may facilitate folding or bending of the planar surface 164, 166 around the actuation device 172 allowing a fixation feature more central to the planar surface 164, 166 (e.g., teeth) to also engage the facet surface.

The distraction mechanism 160 in this embodiment can be removably or permanently mounted on the distal end of an insertion tool 159 so it can be removed from the insertion tool 159 and left in the distracted joint 36 as a permanent implant or removed from the distracted joint 36 after an auxiliary implant is positioned therein.

Figure 17A:
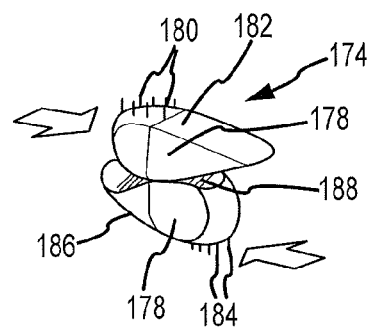
FIG. 17A is an isometric of a twelfth embodiment of a distraction device in accordance with the present invention.
Figure 17B:
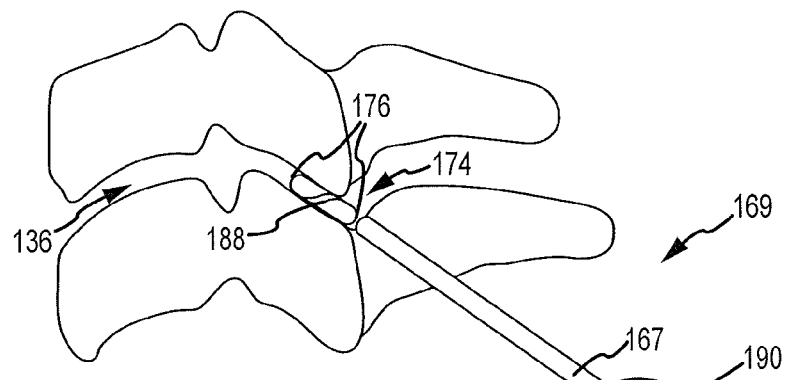
FIG. 17B is a side view of the device of FIG. 17A positioned in a facet joint and on the end of an insertion tool.
Figure 17C:
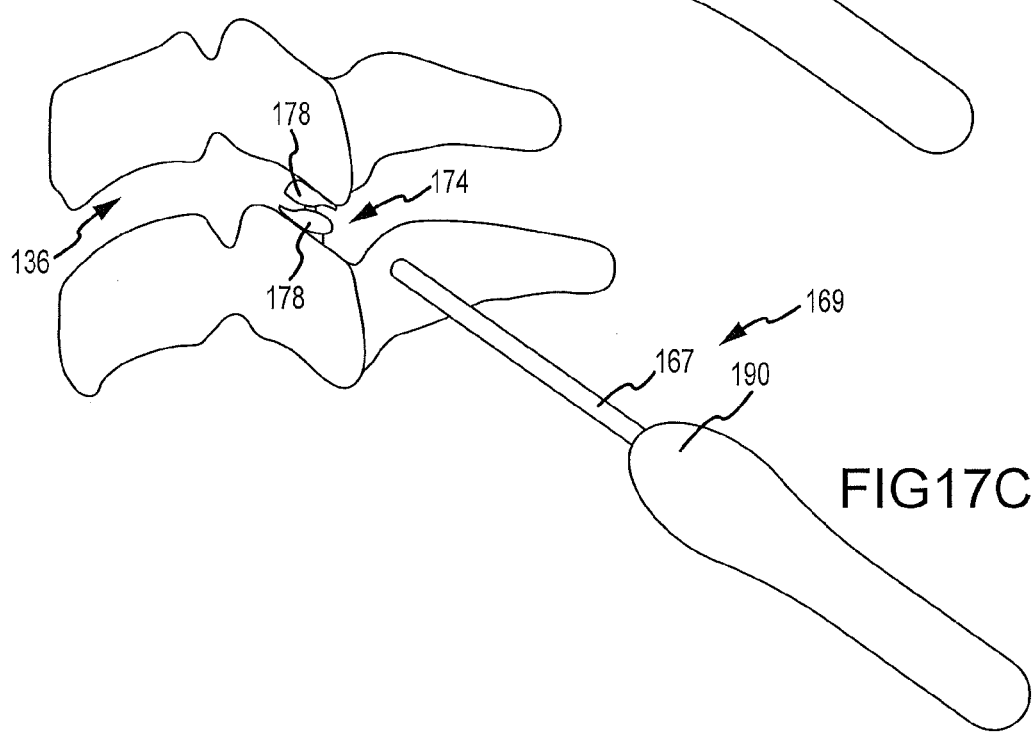
FIG. 17C is a side view similar to FIG. 17B with the device of FIG. 17A having been expanded and the insertion tool separated therefrom to leave the device as an implant in a distracted facet joint.

With reference to FIGS. 17A-17C, a twelfth embodiment of the invention is illustrated. As best appreciated by reference to FIGS. 17A and 17B, the distraction mechanism 174 can be configured like a medical capsule (FIG. 17B) so as to be cylindrical in configuration with rounded leading and trailing ends 176. The mechanism 174 can be formed from two generally ovular or tear-drop shaped components with an upper component 182 having fixation mechanisms 180 on its upper surface and the lower component 186 having fixation mechanisms 180 on its lower surface. The components can be slidably related along a diagonal plane 188 of separation.

In use, the mechanism 174 can be inserted into the facet joint 36 with a delivery tool 169 having the mechanism 174 positioned on its distal end. As the mechanism 174 is advanced, the fixation elements 184 can grip the opposing facet surfaces causing the tear-drop components 182, 186 to translate along the diagonal plane 188 in one direction or the other. In one direction, of course, the implant becomes longer with a maximum height of the diameter of the capsule as seen in FIG. 17B while in an opposite direction the components 182, 186 slidably converge along the diagonal plane 188 so that the implant is cammed into a taller or thicker dimension causing more distraction of the joint 36. The mechanism 174 can have any number or type of fixation mechanisms 180 on the top and bottom surfaces to prevent migration.

The opposing surfaces along the diagonal plane 188 can be somewhat smooth to prevent excessive friction while facilitating small amounts of motion along the diagonal plane 188 once the mechanism 174 is permanently fixed against the superior and inferior facet surfaces.

The mechanism 174 can be made of steel, titanium, PEEK, silicone, plastic, polymer, or nitinol. The mechanism 174 can be detachable to facilitate permanent implantation, but, as with the other embodiments, can be removed once an auxiliary implant is positioned upon distraction of the joint 36 with the mechanism 174.

A thirteenth embodiment of a distraction mechanism 192 of the invention is shown in FIGS. 18A and 18B. The mechanism 192 of this embodiment can include a polyethylene balloon 194 mounted at the distal end of a delivery tool. The distal end of the delivery tool within the balloon 194 can include a large conduit 198 with two separated enclosed vessels 200, 202 and an output port 204 on the bottom of the device communicating with an inlet vessel 200 and an intake port 206 on the top of the device communicating with a return vessel 202. Fluid can be injected into the balloon 194 through the inlet vessel 200 and removed as desired through the return vessel 202 as shown by the directional arrows in FIGS. 18A and 18B.

In use, the balloon 194 can be positioned within the facet joint 36 and the balloon 194 can be inflated through the introduction of a contrast medium fluid. Pressure within the balloon 194 can be developed through further injection of fluid and thus the pressure can cause expansion of the balloon 194 structure. The balloon 194 expansion can cause separation of the facet joint 36 resulting in distraction and forward translation of the joint 36.

Once in place and expanded, as with other distraction mechanisms, the mechanism 192 can be detached from the tool and used as an implant or the mechanism 192 can be used to hold the distraction of the joint 36 while another implant is placed. Where used as implant, the balloon 194 can be filled with a bio-inert hydrogel once optimal distraction and translation of the facet joint 36 is achieved. Also, a sealing valve at the proximal aspect of the balloon 194 can be provided to prevent leaking of the hydrogel. Alternatively or additionally, the balloon 194 can be inflated with a fast-curing silicone when used as a permanent implant.

In another embodiment of the balloon 194 (not shown), the balloon 194 can be forked shaped having two legs and a recess therebetween in which a permanent implant of any of the types previously described, or to be later described, can be positioned. In this configuration, the balloon 194 can be inflated to achieve optimal distraction and translation, but can be removed following the successful placement and fixation of the permanent implant.

A fourteenth embodiment of a distraction mechanism 208 of the invention is shown in FIGS. 19A and 19B and operates similarly to that of the thirteenth embodiment shown in FIGS. 18A and 18B. In the fourteenth embodiment, the main conduit 210 on the distal end of the delivery tool can have a large enclosed channel 214 formed therein and a smaller enclosed channel 216 communicating with the large channel. The large channel 214 can have an extended cylindrical vessel 218 protruding beyond the end of the main conduit and a rounded tip 220 with a lateral outlet port 222 in a recess 224 formed in a side thereof. A balloon 226 can be sealed to the large vessel 210 so that fluids emitted through the outlet port 222 can fill and expand the balloon 226 to distract the facet joint 36 as with the thirteenth embodiment, and the smaller enclosed channel 216 can be used to remove fluid from the balloon 226 as desired.

Figure 20A:
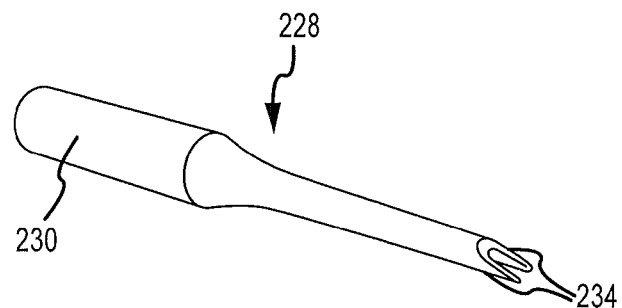
FIG. 20A is an isometric of a fifteenth embodiment of a distraction device in accordance with the present invention.
Figures 20B, 20C:
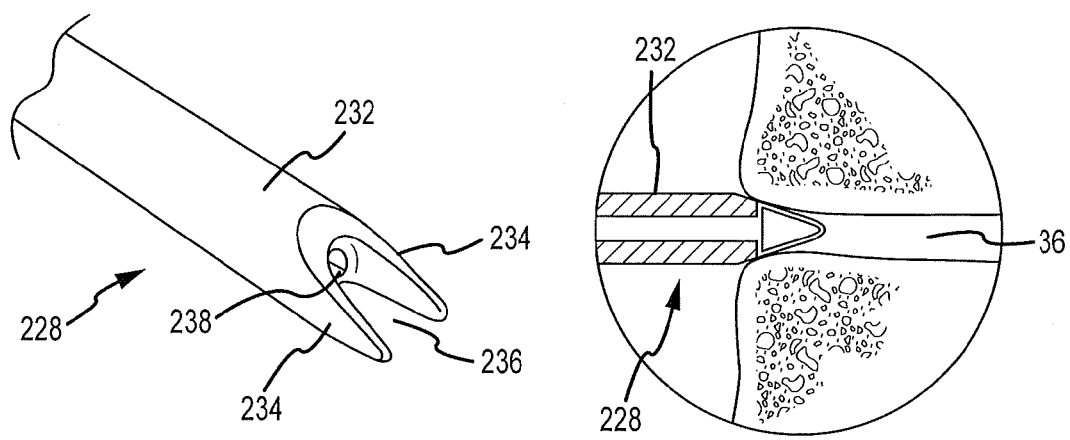
FIG. 20B is an enlarged fragmentary isometric view of the distal tip of the device of FIG. 20A.
FIG. 20C is a diagrammatic vertical section showing the device of FIG. 20A inserted into a facet joint.

A fifteenth embodiment of the distraction mechanism 228 of the invention is shown in FIGS. 20A-20C. The mechanism 228 can again be mounted on the distal end of a delivery tool with the mechanism 228 being a hollow cylinder 232 having tapered diametrically opposed protruding prongs 234 at its leading end. The prongs 234 can define a recess 236 therebetween and a hollow interior of the device can communicate with an injection port 238 positioned between the prongs 234. The tapered prongs 234 can be advanced into a facet joint 36 to spread the joint 36 apart to allow room to inject fluid through the injection port 238. The injection port 238 can be used for communicating a stylet to the facet joint 36 or for introducing materials (including bone graft, BMP, OP1, silicone, PMMA bone cement, or hydrogel) and permanent implants to provide permanent distraction and translation.

Figure 21A:
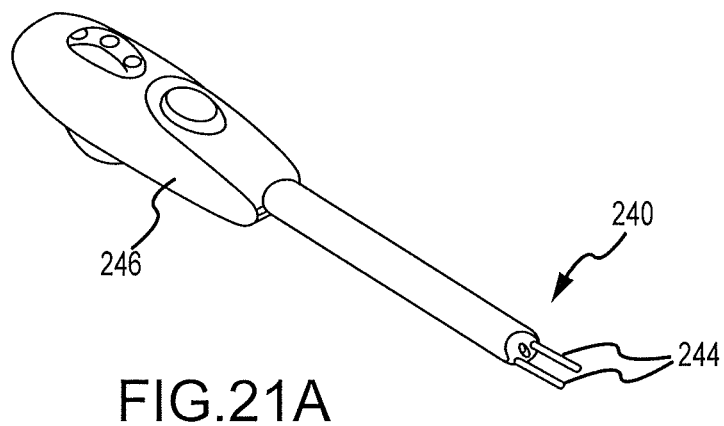
FIG. 21A is an isometric of a sixteenth embodiment of a distraction device in accordance with the present invention.
Figure 21B:
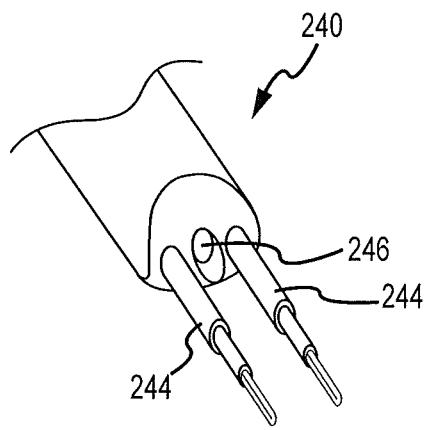
FIG. 21B is an enlarged fragmentary isometric of the distal tip of the device of FIG. 21A.
Figure 21C:
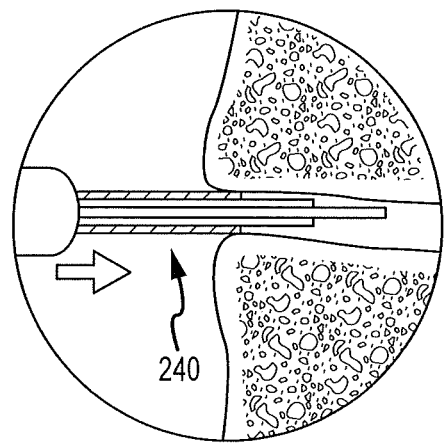
FIG. 21C is a diagrammatic vertical section showing the device of FIG. 21A inserted into a facet joint.

A sixteenth embodiment of the distraction mechanism 240 of the invention is shown in FIGS. 21A-21C with this mechanism 240 again being mounted on a delivery tool. The mechanism 240 can include a pair of parallel tubular members 244 on lateral aspects of the distal tip of the delivery tool and a port 246 between the tubular members 244 communicating with the hollow interior of the delivery tool. Each tubular member 244 can have a relatively small leading end but become progressively larger as bigger tubes are telescoped over the smaller tubes. The larger tubes can cause increasing separation of the facet joint 36 resulting in distraction and forward translation. The port can facilitate the introduction of subsequent instruments, stylets, materials (including bone graft, BMP, OP1, silicone, PMMA bone cement, hydrogel) and permanent implants to provide permanent distraction and translation.

Figure 22A:
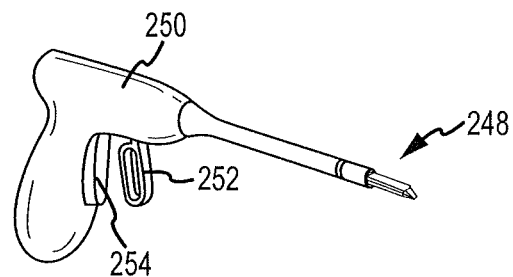
FIG. 22A is an isometric of a seventeenth embodiment of the distraction device of the present invention.
Figure 22B:
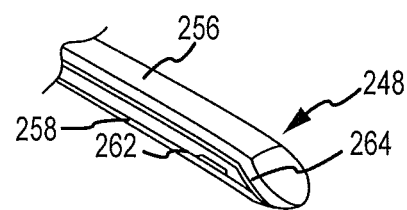
FIG. 22B is an enlarged fragmentary isometric of the distal tip of the device of FIG. 22A in a closed position.
Figure 22C:
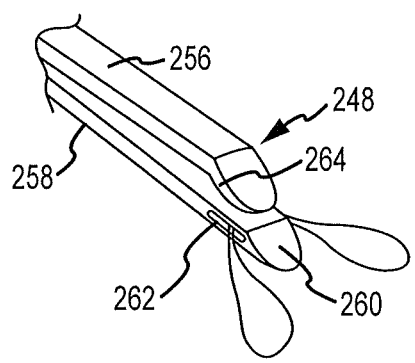
FIG. 22C is a fragmentary isometric similar to FIG. 22B with the tip in an expanded position.
Figure 22D:
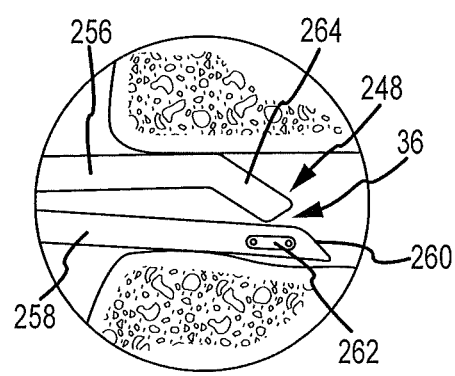
FIG. 22D is a diagrammatic vertical section showing the device in the expanded condition of FIG. 22C inserted into a facet joint.
Figure 23A:
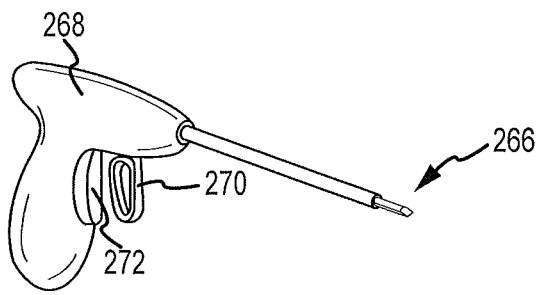
FIG. 23A is an isometric of an eighteenth embodiment of the distraction device in accordance with the present invention.
Figure 23B:
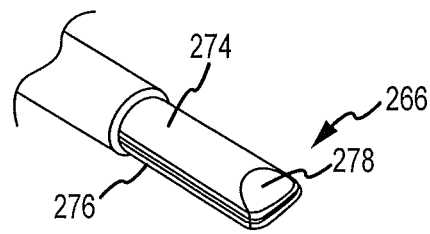
FIG. 23B is an enlarged fragmentary isometric showing the tip of the device of FIG. 23A in a closed position.
Figure 23C:
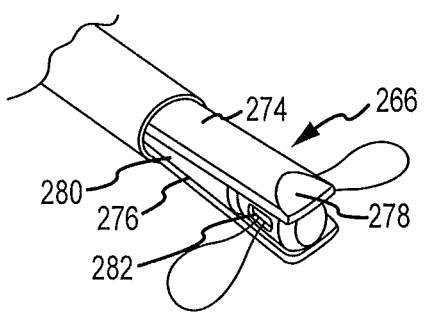
FIG. 23C is a fragmentary isometric similar to FIG. 23B with the tip in an expanded position.
Figure 23D:
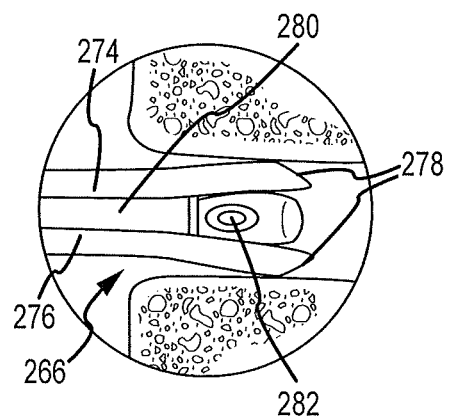
FIG. 23D is a diagrammatic vertical section showing the device in the expanded position of FIG. 23C inserted into a facet joint.
Figure 24A:
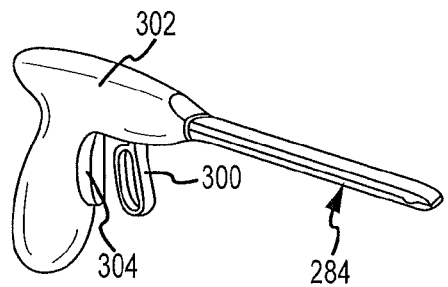
FIG. 24A is an isometric of a nineteenth embodiment of the distraction device of the invention.
Figure 24B:
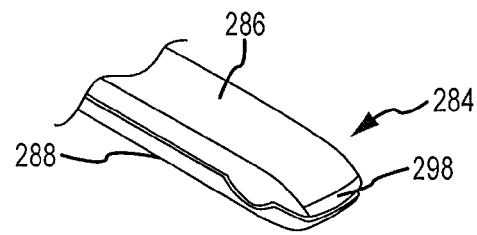
FIG. 24B is an enlarged fragmentary isometric of the tip of the device of FIG. 24A in a closed position.
Figure 24C:
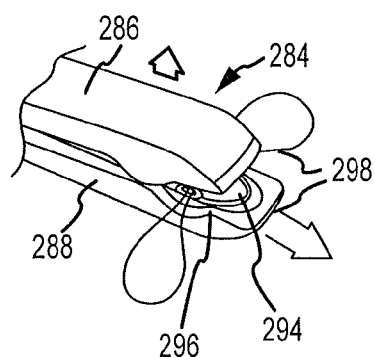
FIG. 24C is a fragmentary isometric similar to FIG. 24B with the tip expanded.
Figure 24D:
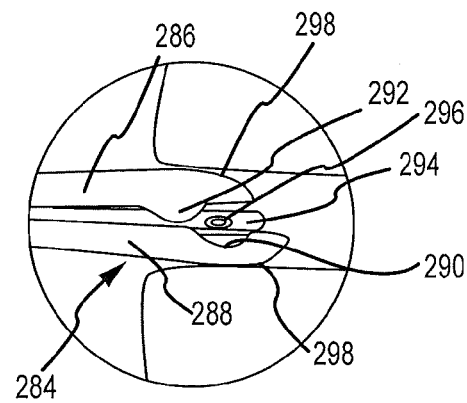
FIG. 24D is a diagrammatic vertical section showing the device in the expanded position of FIG. 24C inserted into a facet joint.

A seventeenth embodiment of the invention is shown in FIGS. 22A-22D. In this embodiment, the distraction mechanism 248 is mounted on the tip of a delivery tool having dual triggers 252, 254 for delivering energy to the mechanism 248. The mechanism 248, as seen best in FIGS. 22B-22D, can include upper and lower arms 256, 258 having confronting flat faces with at least the upper arm being somewhat flexible while both arms are substantially rigid. The lower arm 258 can have a rearwardly and upwardly beveled leading tip 260 and a hollow interior in communication with side ports 262 on opposite sides of the arm 258. The upper arm 256 can have a relatively flat main body which overlies in confronting relationship the lower arm 258 with the upper arm 256 having a downwardly and forwardly inclined leg 264 which conforms with the bevel of the lower arm 258. When the upper and lower arms 256, 258 are collapsed, as shown in FIG. 22B, they lie in confronting contiguous relationship with the leading edge of the upper arm 256 being close to the elevation of the lower edge of the lower arm 258 so as to provide a thin profile for insertion into a facet joint 36. One trigger on the delivery tool can retract the upper arm 256 so that the inclined leg 264 at the leading end thereof is cammed upwardly onto the top of the lower arm 258 by the leading beveled edge 260 of the lower arm 258. The retraction of the upper arm 256 can separate the upper arm 256 from the lower arm 258 as shown best in FIGS. 22C and 22D so that when they are positioned within the facet joint 36, a distraction of the joint 36 can be achieved. Once the joint 36 is distracted to the desired degree, the introduction of instruments, stylets, materials (including bone graft, BMP, OP1, silicone, PMMA bone cement, hydrogel) or other permanent implants of the type previously disclosed herein can be introduced through the side ports 262 with the second trigger to provide permanent distraction and translation.

An eighteenth embodiment of the distraction mechanism of the invention is shown in FIGS. 23A-23D. In this embodiment of the invention, the distraction mechanism 266 can again be mounted on the distal end of a delivery tool having dual triggers 270, 272. The mechanism 266 can have upper and lower blades 274, 276 each having forwardly tapered leading ends 278 so as to define a relatively thin leading tip resembling an elongated duckbill. The tip of the duckbill for the mechanism 266 can be thin enough or flat enough to access the facet joint 36. Once the mechanism 266 is positioned within the facet joint 36, a distraction energy can be applied to the mechanism 266 by pulling one trigger which causes an internal hollow cylinder 280 having a blunt leading end to advance forwardly thereby separating the upper and lower blades 274, 276. The separation can cause distraction of the facet joint 36 and lateral injection ports 282 can be provided on the internal cylinder through which instruments, stylets, materials (including bone graft, BMP, OP1, silicone, PMMA bone cement, or hydrogel) can be injected into the facet joint 36 by the second trigger or other permanent implants could be introduced to provide permanent distraction and translation.

A nineteenth embodiment of the invention is shown in FIGS. 24A-24D to be similar to the eighteenth embodiment. In the nineteenth embodiment, again, upper and lower relatively rigid yet flexible blades 286, 288 can be provided that in a closed position are contiguous and confronting with each other. Adjacent the leading end 298 of the blades 286, 288 the lower blade 288 can have a transverse cylindrical recess 290 formed therein while the upper blade 286 can have a transverse cylindrical protrusion 294 which seats in the recess 290 to permit the upper and lower blades 286, 288 to be contiguous in the closed position. An internal cylinder 294 having lateral ports 296 at its leading end can be positioned between the blades 286, 288 and confined therebetween when the blades 286, 288 are closed so that tapered forward ends 298 of the blade can be inserted into the facet joint 36. By pulling the first trigger on the delivery tool, the upper blade 286 can be retracted rearwardly so that the cylindrical protrusion 292 is cammed by the cylindrical recess 290 to cause the upper blade 286 to elevate relative to the lower blade 288 thereby distracting the facet joint 36. When the facet joint 36 has been distracted, instruments, stylets, materials (including bone graft, BMP, OP1, silicone, PMMA bone cement, or hydrogel) can be injected into the facet joint 36 with the second trigger or other permanent implants of the types previously disclosed herein could be introduced to provide permanent distraction and translation.

FIGS. 25A-25F disclose various embodiments of permanent implants which can be inserted into a facet joint 36, for example, with a delivery tool of the type disclosed in the tenth embodiment or any other of the embodiments disclosed herein if such embodiments are supplemented with an integral delivery lumen and push rod configuration. Alternatively, the various embodiments of the above-described distraction mechanisms can be positioned in a facet joint 36 to retain the joint 36 in a distracted position, a translated position, or a combination distracted and translated position until a permanent implant can be positioned in the distracted joint 36 separately via a separate delivery device or tool.

Figure 25A:
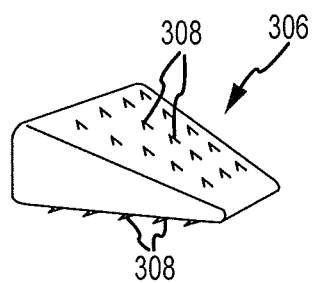
FIG. 25A is an isometric of a first embodiment of an implant for delivery with or in conjunction with a distraction device.

FIG. 25A shows a permanent implant 306 that is of wedge shape having fixation mechanisms 308 on the top and bottom surfaces comprised of teeth all directed in a common direction toward the trailing end of the implant. The wedge shape can facilitate distraction that is both normal to the facet surfaces and parallel to the facet surfaces. In other words, the wedge shape can separate the facet surfaces from each other in a direction that is perpendicular and a direction that is parallel to the facet surfaces, thus both increasing the offset distance between the facet surfaces and translating the facet surfaces relative to each other. This combination of displacement can more fully open the foraminal spaces.

Figure 25B:
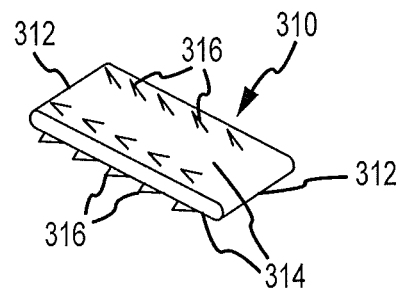
FIG. 25B is an isometric of a second embodiment of an implant.

FIG. 25B shows another implant 310 having rounded leading and trailing ends 312 and flat upper and lower parallel surfaces 314, again with teeth on both the upper and lower surfaces 314, which are inclined rearwardly.

Figure 25C:
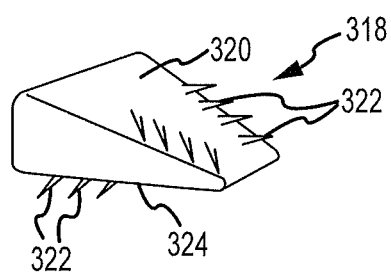
FIG. 25C is an isometric of a third embodiment of an implant.

FIG. 25C discloses another wedge-shaped embodiment of a permanent implant 318 where the upper surface 320 of the wedge has teeth 322 directed forwardly and outwardly along opposite lateral edges at the leading edge of the wedge while the bottom surface 324 has similar teeth 322 at the trailing end of the wedge directed rearwardly and outwardly. The oppositely oriented teeth 322 may enhance and help to maintain the translation displacement already provided by the wedge shape.

Figure 25D:
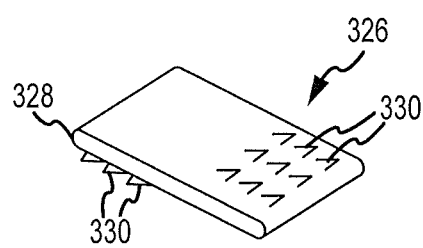
FIG. 25D is an isometric of a fourth embodiment of an implant.

FIG. 25D shows a permanent implant 326 configured similarly to FIG. 25B with the trailing end 328 being squared off rather than rounded and with teeth 330 across the top of the leading end directed forwardly and teeth 330 across the bottom and the trailing end directed rearwardly. The oppositely oriented teeth 330 may provide a translation displacement.

Figure 25E:
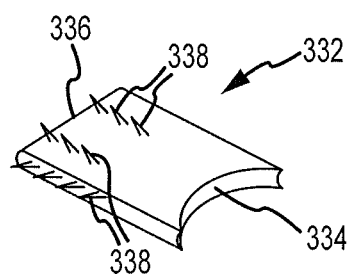
FIG. 25E is an isometric of a fifth embodiment of an implant.
Figure 25F:
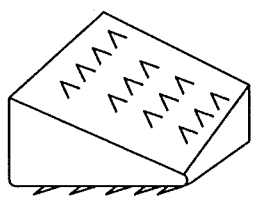
FIG. 25F is an isometric of a sixth embodiment of an implant.

FIG. 25E shows still another implant 332 of generally rectangular configuration but having a concave leading end 334 and a rounded trailing end 336. The implant 332 has rearwardly directed fixation mechanisms 338 in the form of teeth along the upper surface on lateral sides and along the side walls.

Permanent implants can vary in geometry, material, and fixation mechanism. For example with respect to geometry a wedge shaped implant can provide for a greater height of the posterior aspect of the implant relative to the anterior aspect of the implant. The wedge can also provide for uniform dimensions at the lateral and medial aspects of the implant. The wedge shape may result in a translating vector force and a separating vector force that results in both subluxation and distraction, thereby increasing the foraminal space more fully as discussed in U.S. provisional patent application No. 61/059,723, filed Jun. 6, 2008, and incorporated by reference herein in its entirety. A double wedged implant can provide greater height of the posterior aspect of the implant relative to the anterior aspect of the implant in addition to greater height of the lateral aspect of the implant relative to the medial aspect of the implant (see FIG. 25F). Other geometrical variations can include a flat rectangular shape, an oval pill shape, a concave superior surface, a concave inferior surface, a convex superior surface, a convex inferior surface, a convex anterior surface, a concave anterior surface, a convex posterior surface, and a concave posterior surface.

With respect to materials, several materials can be provided including steel, PEEK, carbon, allograft, polymer, and silicone. With respect to fixation mechanisms, at least three mechanisms can be included. Aggressive shark teeth can be provided with a directional orientation positioned to achieve optimal fixation relative to the natural biomechanics of various sections of the spine. The teeth can be long enough to gain purchase in the cortical bone of the facet surfaces. Cleats can also be provided that have a less aggressive profile than the shark teeth but still allow for directional orientation for the same reasons described above. These cleats can also be capable of anchoring in the hard cortical bone of the facet surface. Additionally, a roughened pore surface can be provided to prevent free sliding of the implant within the facet joint 36. These surfaces can be roughened and coated with commercially available resurface chemicals that would create friction and prevent device migration.

Any or all of the implants can be adapted as fusion type implants or motion preservation type devices. Implants with varying degrees of motion preservation can also be provided. In the case of a motion preservation type implant, the implant can have fixation mechanisms on one side to enable both temporary and permanent fixation to one surface of the facet joint 36 while allowing the opposing facet surface to slide freely across the surface of the implant. The facet joint 36 can be a naturally sliding joint 36 and a distraction implant with fixation on only one side may accommodate the natural sliding of the facet. However, in some circumstances, a fusion type implant can be more suitable. In these circumstances the implant can include fixation mechanisms on both sides of the of the implant.

Figure 26A:
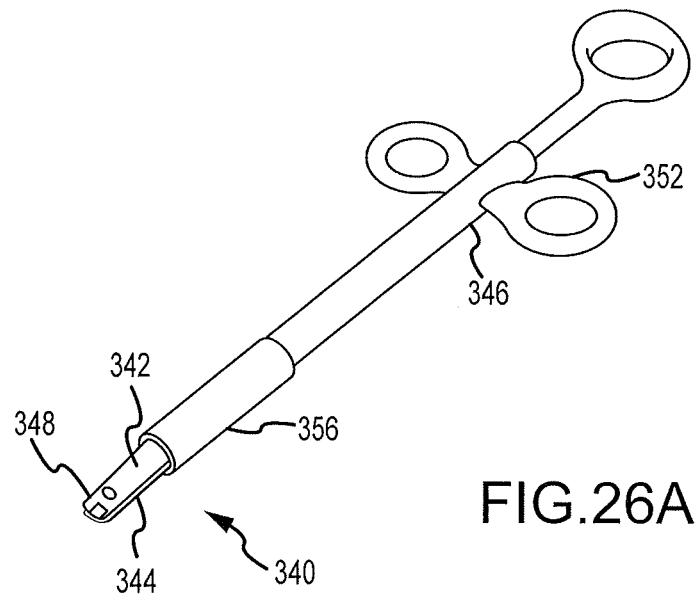
FIG. 26A is an isometric of a twentieth embodiment of the distraction device in accordance with the present invention.
Figure 26B:
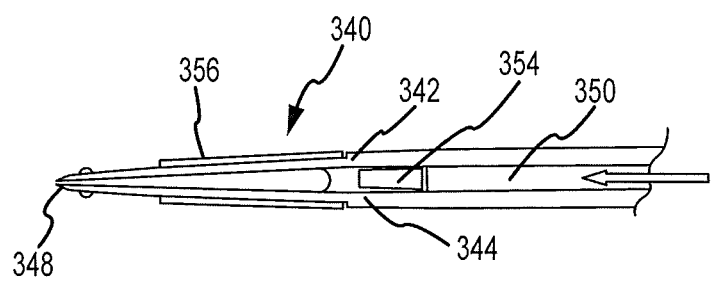
FIG. 26B is a vertical section through the distal tip of the device of FIG. 26A in a closed position.
Figure 26C:
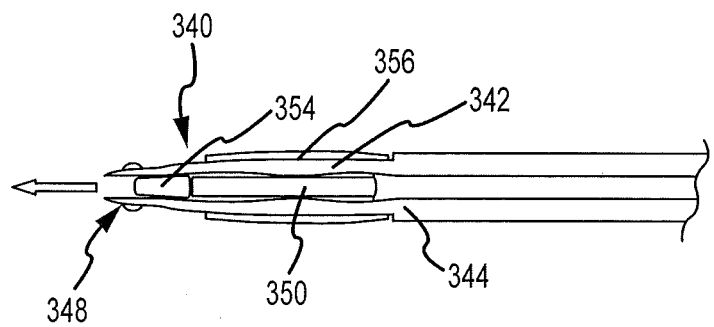
FIG. 26C is a vertical section similar to FIG. 26A with the distal tip expanded.

FIGS. 26A-26C disclose a twentieth embodiment of a distraction mechanism of the invention which is somewhat similar to the embodiments of FIGS. 22A-D and 23A-D. In this embodiment of the invention, upper and lower confronting bars 342, 344, which are relatively rigid but have flexibility, can be retained in a delivery tool so that the leading tip 348 of the distraction mechanism 340 is of a duckbill structure with the leading tip 348 of both the upper and lower bars 342, 344 being beveled to form a thin leading end of the mechanism 340 which can be inserted into the facet joint 36. The upper and lower bars 342, 344 can define a longitudinal channel therebetween in which a plunger 350 can be slidably disposed and reciprocally moved with a finger grip 352 on the delivery tool. Forwardly of the plunger 350, a permanent implant 354 can be positioned within the channel between the upper and lower bars 342, 344 so that upon forward movement of the plunger 350, the implant 354 can spread the upper and lower bars 342, 344 allowing the implant 354 to be released from the leading end 348 of the distraction mechanism 340 and be deposited in the facet joint 36. The upper and lower bars 342, 344 can be biased toward each other by an elastic band 356 which passes around the upper and lower bars 342, 344 forwardly of the delivery tool but rearwardly of the leading tip 348 of the distraction mechanism 340.

Although the present invention has been described with a certain degree of particularity, it is understood the disclosure has been made by way of example, and changes in detail or structure may be made without departing from the spirit of the invention as defined in the appended claims. In particular, it is noted that several embodiments have been described with particular features. It is to be understood that the features of any given embodiment can be combined with features of other embodiments and still be within the scope of the invention. For example, the elongate member of FIGS. 9A-9C has been described as a toothed member adapted for a ratcheting action, while in other embodiments the elongate member has been described as a threaded member. Where functionality allows, interchanging certain features of one embodiment with another embodiment is within the scope of the present invention.

What is claimed is:

1. A method for distracting a facet joint formed by two adjacent vertebrae of a spine of patient, the method comprising:
   advancing a facet distraction implant into the patient and toward the facet joint in a posterior-to-anterior direction, relative to the patient;
   delivering the facet distraction implant in an insertion configuration into the facet joint, wherein the facet distraction implant comprises an upper surface, a lower surface, and multiple fixation features disposed along the upper and lower surfaces; and
   inserting an actuation device into the facet distraction implant to distract the facet joint.

2. The method of claim 1, wherein the method is performed minimally invasively.

3. The method of claim 1, wherein the method is performed percutaneously.

4. The method of claim 1, wherein the advancing and delivering steps are performed by advancing and delivering the facet distraction implant through a cannula.

5. The method of claim 1, wherein the actuation device is a wedge-like member.

6. The method of claim 1, wherein the upper and lower surfaces are planar.

7. The method of claim 1, wherein the multiple fixation features comprise a tapered keel.

8. The method of claim 1, wherein the multiple fixation features comprise teeth.

9. The method of claim 1, wherein at least one of the upper surface or the lower surface includes a slot.

10. The method of claim 9, wherein the actuation device comprises an elongate threaded member, wherein the threaded member includes a thread adapted to engage the slot, and wherein inserting the actuation device into the facet distraction device comprises advancing the threaded member between the upper and lower surfaces.

11. The method of claim 10, wherein inserting the actuation device further comprises threading the threaded member through the slot such that a portion of the threaded member protrudes through the slot.

12. The method of claim 11, wherein the threaded member protrudes through the slot sufficiently to prevent the facet distraction device from backing out of the facet joint.

13. The method of claim 1, wherein at least one of the supper surface of the lower surface is generally planar and configured to bend around the actuation device when the actuation device is inserted into the facet distraction device.

14. The method of claim 1, wherein the facet distraction device is wedge-shaped.

15. The method of claim 1, wherein at least one of the upper surface or the lower surface of the facet distraction device is generally planar and includes a malleable material that facilitates the at least one of the surfaces conforming to the facet joint upon implantation.

16. The method of claim 1, wherein the upper surface and the lower surface are connected at one end.

\* \* \* \* \*

UNITED STATES PATENT AND TRADEMARK OFFICE
CERTIFICATE OF CORRECTION

PATENT NO. : 9,622,874 B2
APPLICATION NO. : 13/949042
DATED : April 18, 2017
INVENTOR(S) : Bruce M. McCormack et al.

It is certified that error appears in the above-identified patent and that said Letters Patent is hereby corrected as shown below:

In the Claims

At Column 23, Line 1, Claim 10, Line 5:
"distraction device"
Should Read:
--distraction implant--

At Column 23, Line 9, Claim 12, Line 3:
"distraction device"
Should Read:
--distraction implant--

At Column 23, Line 11, Claim 13, Line 2:
"supper"
Should Read:
--upper--

At Column 23, Line 11, Claim 13, Line 2:
"supper surface of"
Should Read:
--upper surface or--

At Column 23, Line 13, Claim 13, Line 4:
"distraction device"
Should Read:
--distraction implant--

Signed and Sealed this
Tenth Day of October, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,622,874 B2

At Column 23, Line 15, Claim 14, Line 2:
"device"
Should Read:
--implant--

At Column 23, Line 18, Claim 15, Line 3:
"device"
Should Read:
--implant--